United States Patent
Lim et al.

(10) Patent No.: US 11,974,611 B2
(45) Date of Patent: May 7, 2024

(54) METHOD FOR CONTROLLING TEMPERATURE OF HEATER INCLUDED IN AEROSOL GENERATION DEVICE ACCORDING TO TYPE OF CIGARETTE, AND AEROSOL GENERATION DEVICE FOR CONTROLLING TEMPERATURE OF HEATER ACCORDING TO TYPE OF CIGARETTE

(71) Applicant: KT&G CORPORATION, Daejeon (KR)

(72) Inventors: Hun Il Lim, Seoul (KR); Dong Sung Kim, Yongin-si (KR); Ji Hun Song, Gunsan-si (KR)

(73) Assignee: KT&G CORPORATION, Daejeon (KR)

( * ) Notice: Subject to any disclaimer, the term of this patent is extended or adjusted under 35 U.S.C. 154(b) by 22 days.

(21) Appl. No.: 16/759,829

(22) PCT Filed: May 21, 2018

(86) PCT No.: PCT/KR2018/005767
§ 371 (c)(1),
(2) Date: Apr. 28, 2020

(87) PCT Pub. No.: WO2019/088382
PCT Pub. Date: May 9, 2019

(65) Prior Publication Data
US 2020/0305512 A1    Oct. 1, 2020

(30) Foreign Application Priority Data

Oct. 30, 2017  (KR) .................. 10-2017-0142578
Nov. 6, 2017   (KR) .................. 10-2017-0146972

(Continued)

(51) Int. Cl.
*A24F 40/57* (2020.01)
*A24F 40/53* (2020.01)
(Continued)

(52) U.S. Cl.
CPC .............. *A24F 40/57* (2020.01); *A24F 40/53* (2020.01); *A24F 40/65* (2020.01); *H05B 1/0297* (2013.01); *A24F 40/20* (2020.01)

(58) Field of Classification Search
CPC ....................................................... A24F 40/57
See application file for complete search history.

(56) References Cited

U.S. PATENT DOCUMENTS

| 5,348,027 A | 9/1994 | Barnes et al. |
| 5,388,594 A | 2/1995 | Counts et al. |

(Continued)

FOREIGN PATENT DOCUMENTS

| CA | 2 778 903 A1 | 5/2011 |
| CA | 2 970 045 A1 | 6/2016 |

(Continued)

OTHER PUBLICATIONS

Translation of KR 20160009678 (Year: 2016).*

(Continued)

*Primary Examiner* — Cynthia Szewczyk
(74) *Attorney, Agent, or Firm* — Sughrue Mion, PLLC

(57) ABSTRACT

Provided is a method of controlling a temperature of a heater included in an aerosol generation device according to a type of cigarette. The method includes receiving temperature profiles of different types of cigarette from a user terminal; sensing a cigarette coupled to the heater after receiving the temperature profiles; identifying a type of the sensed cigarette; selecting a temperature profile corresponding to the identified type from among the temperature profiles; and (Continued)

controlling power supplied from a battery to the heater according to the selected temperature profile.

8 Claims, 9 Drawing Sheets

(30) Foreign Application Priority Data

Nov. 22, 2017 (KR) ........................ 10-2017-0156729
May 4, 2018 (KR) ........................ 10-2018-0052133

(51) Int. Cl.
 *A24F 40/65* (2020.01)
 *H05B 1/02* (2006.01)
 *A24F 40/20* (2020.01)

(56) References Cited

U.S. PATENT DOCUMENTS

| | | | |
|---|---|---|---|
| 5,408,574 A | 4/1995 | Deevi et al. |
| 5,505,214 A | 4/1996 | Collins et al. |
| 5,555,476 A | 9/1996 | Suzuki et al. |
| 5,665,262 A | 9/1997 | Hajaligol et al. |
| 5,692,525 A | 12/1997 | Counts et al. |
| 5,723,228 A | 3/1998 | Okamoto |
| 5,750,964 A | 5/1998 | Counts et al. |
| 5,878,752 A | 3/1999 | Adams et al. |
| 5,902,501 A | 5/1999 | Nunnally et al. |
| 5,934,289 A | 8/1999 | Watkins et al. |
| 5,949,346 A | 9/1999 | Suzuki et al. |
| 5,970,719 A | 10/1999 | Merritt |
| 6,026,820 A | 2/2000 | Baggett, Jr. et al. |
| 6,615,840 B1 | 9/2003 | Fournier et al. |
| 6,803,550 B2 | 10/2004 | Sharpe et al. |
| 6,810,883 B2 | 11/2004 | Felter et al. |
| 7,082,825 B2 | 8/2006 | Aoshima et al. |
| 7,594,945 B2 | 9/2009 | Kim et al. |
| 7,682,571 B2 | 3/2010 | Kim et al. |
| 7,726,320 B2 | 6/2010 | Robinson et al. |
| 8,205,622 B2 | 6/2012 | Pan |
| 8,558,147 B2 | 10/2013 | Greim et al. |
| 8,602,037 B2 | 12/2013 | Inagaki |
| 8,689,804 B2 | 4/2014 | Fernando et al. |
| 8,833,364 B2 | 9/2014 | Buchberger |
| 8,997,754 B2 | 4/2015 | Tucker et al. |
| 9,084,440 B2 | 7/2015 | Zuber et al. |
| 9,165,484 B2 | 10/2015 | Choi |
| 9,295,286 B2 | 3/2016 | Shin |
| 9,347,644 B2 | 5/2016 | Araki et al. |
| 9,405,148 B2 | 8/2016 | Chang et al. |
| 9,420,829 B2 | 8/2016 | Thorens et al. |
| 9,516,899 B2 | 12/2016 | Plojoux et al. |
| 9,532,600 B2 | 1/2017 | Thorens et al. |
| 9,541,820 B2 | 1/2017 | Ogawa |
| 9,693,587 B2 | 7/2017 | Plojoux et al. |
| 9,713,345 B2 | 7/2017 | Farine et al. |
| 9,814,269 B2 | 11/2017 | Li et al. |
| 9,839,238 B2 | 12/2017 | Worm et al. |
| 9,844,234 B2 | 12/2017 | Thorens et al. |
| 9,848,651 B2 | 12/2017 | Wu |
| 9,854,845 B2 | 1/2018 | Plojoux et al. |
| 9,949,507 B2 | 4/2018 | Flick |
| 9,974,117 B2 | 5/2018 | Qiu |
| 10,070,667 B2 | 9/2018 | Lord et al. |
| 10,104,909 B2 | 10/2018 | Han et al. |
| 10,104,911 B2 | 10/2018 | Thorens et al. |
| 10,136,673 B2 | 11/2018 | Mironov |
| 10,136,675 B2 | 11/2018 | Li et al. |
| 10,143,232 B2 | 12/2018 | Talon |
| 10,238,149 B2 | 3/2019 | Hon |
| 10,390,564 B2 | 8/2019 | Fernando et al. |
| 10,412,994 B2 | 9/2019 | Schennum et al. |
| 10,426,193 B2 | 10/2019 | Schennum et al. |
| 10,548,350 B2 | 2/2020 | Greim et al. |
| 10,555,555 B2 | 2/2020 | Fernando et al. |
| 10,602,778 B2 | 3/2020 | Hu et al. |
| 10,617,149 B2 | 4/2020 | Malgat et al. |
| 10,694,783 B2 | 6/2020 | Jochnowitz |
| 10,701,973 B2 | 7/2020 | Lee |
| 10,757,975 B2 | 9/2020 | Batista et al. |
| 10,842,194 B2 | 11/2020 | Batista et al. |
| 10,973,087 B2 | 4/2021 | Wang et al. |
| 11,051,545 B2 | 7/2021 | Batista et al. |
| 11,051,550 B2 | 7/2021 | Lin et al. |
| 11,147,316 B2 | 10/2021 | Farine et al. |
| 2003/0226837 A1 | 12/2003 | Blake et al. |
| 2004/0089314 A1 | 5/2004 | Felter et al. |
| 2004/0149737 A1 | 8/2004 | Sharpe et al. |
| 2005/0142036 A1 | 6/2005 | Kim et al. |
| 2006/0267614 A1 | 11/2006 | Lee et al. |
| 2007/0007266 A1 | 1/2007 | Sasaki et al. |
| 2007/0074734 A1 | 4/2007 | Braunshteyn et al. |
| 2007/0246382 A1 | 10/2007 | He |
| 2007/0267031 A1 | 11/2007 | Hon |
| 2010/0074616 A1 | 3/2010 | Kewitsch |
| 2010/0313901 A1 | 12/2010 | Fernando et al. |
| 2011/0155718 A1 | 6/2011 | Greim et al. |
| 2011/0226236 A1 | 9/2011 | Buchberger |
| 2011/0234069 A1 | 9/2011 | Chen et al. |
| 2013/0014772 A1 | 1/2013 | Liu |
| 2013/0220466 A1 | 8/2013 | Zandiyeh et al. |
| 2013/0228191 A1 | 9/2013 | Newton |
| 2013/0255675 A1 | 10/2013 | Liu |
| 2013/0319999 A1 | 12/2013 | Plojoux et al. |
| 2013/0340775 A1* | 12/2013 | Juster .................. H04L 12/1827 131/273 |
| 2014/0060554 A1 | 3/2014 | Collett et al. |
| 2014/0069424 A1 | 3/2014 | Poston et al. |
| 2014/0209105 A1 | 7/2014 | Sears et al. |
| 2014/0217085 A1 | 8/2014 | Alima |
| 2014/0261487 A1 | 9/2014 | Chapman et al. |
| 2014/0286630 A1 | 9/2014 | Buchberger |
| 2014/0339509 A1 | 11/2014 | Choi et al. |
| 2014/0345633 A1 | 11/2014 | Talon et al. |
| 2014/0353856 A1 | 12/2014 | Dubief |
| 2015/0020831 A1 | 1/2015 | Weigensberg et al. |
| 2015/0163859 A1 | 6/2015 | Schneider et al. |
| 2015/0223520 A1 | 8/2015 | Phillips et al. |
| 2015/0230521 A1 | 8/2015 | Talon |
| 2015/0282527 A1 | 10/2015 | Henry, Jr. |
| 2015/0327596 A1 | 11/2015 | Alarcon et al. |
| 2016/0103364 A1 | 4/2016 | Nam et al. |
| 2016/0128386 A1 | 5/2016 | Chen |
| 2016/0174613 A1 | 6/2016 | Zuber et al. |
| 2016/0205998 A1 | 7/2016 | Matsumoto et al. |
| 2016/0321879 A1 | 11/2016 | Oh et al. |
| 2016/0324216 A1 | 11/2016 | Li et al. |
| 2016/0331030 A1 | 11/2016 | Ampolini et al. |
| 2016/0345625 A1 | 12/2016 | Liu |
| 2016/0363570 A1* | 12/2016 | Blackley ............ A61M 15/0003 |
| 2017/0020195 A1 | 1/2017 | Cameron |
| 2017/0042227 A1 | 2/2017 | Gavrielov et al. |
| 2017/0049155 A1 | 2/2017 | Liu |
| 2017/0055589 A1 | 3/2017 | Fernando et al. |
| 2017/0105454 A1 | 4/2017 | Li et al. |
| 2017/0119051 A1 | 5/2017 | Blandino et al. |
| 2017/0119053 A1 | 5/2017 | Henry, Jr. et al. |
| 2017/0143041 A1 | 5/2017 | Batista et al. |
| 2017/0188634 A1 | 7/2017 | Plojoux et al. |
| 2017/0197043 A1 | 7/2017 | Buchberger |
| 2017/0197046 A1 | 7/2017 | Buchberger |
| 2017/0214261 A1 | 7/2017 | Gratton |
| 2017/0238609 A1 | 8/2017 | Schlipf |
| 2017/0295844 A1 | 10/2017 | Thevenaz et al. |
| 2017/0303598 A1 | 10/2017 | Li et al. |
| 2017/0325505 A1 | 11/2017 | Force et al. |
| 2017/0347715 A1 | 12/2017 | Mironov et al. |
| 2018/0027878 A1 | 2/2018 | Dendy et al. |
| 2018/0028993 A1 | 2/2018 | Dubief |
| 2018/0043114 A1* | 2/2018 | Bowen .................. A24F 40/60 |
| 2018/0049471 A1 | 2/2018 | Holoubek et al. |
| 2018/0160733 A1 | 6/2018 | Leadley et al. |
| 2018/0199630 A1 | 7/2018 | Qiu |

(56) References Cited

U.S. PATENT DOCUMENTS

| | | | |
|---|---|---|---|
| 2019/0059448 A1 | 2/2019 | Talon | |
| 2019/0159524 A1 | 5/2019 | Qiu | |
| 2019/0261682 A1* | 8/2019 | Gimkiewicz | ........... A24F 40/40 |
| 2019/0281896 A1 | 9/2019 | Chapman et al. | |
| 2020/0093177 A1 | 3/2020 | Han et al. | |
| 2020/0093185 A1 | 3/2020 | Lim | |
| 2020/0094997 A1 | 3/2020 | Menon et al. | |
| 2020/0154765 A1 | 5/2020 | Lee et al. | |
| 2020/0196670 A1 | 6/2020 | Alarcon et al. | |
| 2020/0260790 A1 | 8/2020 | Kaufman et al. | |
| 2020/0261000 A1 | 8/2020 | Kim et al. | |
| 2020/0305240 A1 | 9/2020 | Holoubek et al. | |
| 2020/0329772 A1 | 10/2020 | Kim et al. | |
| 2020/0359681 A1 | 11/2020 | Han et al. | |
| 2020/0404969 A1 | 12/2020 | Zuber et al. | |
| 2021/0146067 A1 | 5/2021 | Buchberger | |

FOREIGN PATENT DOCUMENTS

| | | | |
|---|---|---|---|
| CN | 1078621 A | 11/1993 | |
| CN | 1126425 A | 7/1996 | |
| CN | 1190335 A | 8/1998 | |
| CN | 1280661 A | 1/2001 | |
| CN | 1491598 A | 4/2004 | |
| CN | 1633247 A | 6/2005 | |
| CN | 1871987 A | 12/2006 | |
| CN | 101277622 A | 10/2008 | |
| CN | 101301963 A | 11/2008 | |
| CN | 101324490 A | 12/2008 | |
| CN | 201253138 Y | 6/2009 | |
| CN | 101518361 A | 9/2009 | |
| CN | 201314692 Y | 9/2009 | |
| CN | 101557728 A | 10/2009 | |
| CN | 101637308 A | 2/2010 | |
| CN | 201657047 U | 11/2010 | |
| CN | 201996322 U | 10/2011 | |
| CN | 102264251 A | 11/2011 | |
| CN | 102595943 A | 7/2012 | |
| CN | 202385727 U | 8/2012 | |
| CN | 102665459 A | 9/2012 | |
| CN | 202854031 U | 4/2013 | |
| CN | 103099319 A | 5/2013 | |
| CN | 202907797 U | 5/2013 | |
| CN | 203040065 U | 7/2013 | |
| CN | 103271447 A | 9/2013 | |
| CN | 103477252 A | 12/2013 | |
| CN | 103519351 A | 1/2014 | |
| CN | 103653257 A | 3/2014 | |
| CN | 103653258 A | 3/2014 | |
| CN | 203492793 U | 3/2014 | |
| CN | 103720056 A | 4/2014 | |
| CN | 103889258 A | 6/2014 | |
| CN | 103974635 A | 8/2014 | |
| CN | 103974638 A | 8/2014 | |
| CN | 103974640 A | 8/2014 | |
| CN | 103997922 A | 8/2014 | |
| CN | 104146353 A | 11/2014 | |
| CN | 104188110 A | 12/2014 | |
| CN | 104219973 A | 12/2014 | |
| CN | 204120226 U | 1/2015 | |
| CN | 204132401 U | 2/2015 | |
| CN | 204146340 U | 2/2015 | |
| CN | 104423130 A | 3/2015 | |
| CN | 204317492 U | 5/2015 | |
| CN | 204393344 U | 6/2015 | |
| CN | 204483007 U | 7/2015 | |
| CN | 104886776 A | 9/2015 | |
| CN | 105188430 A | 12/2015 | |
| CN | 204838003 U | 12/2015 | |
| CN | 105326092 A | 2/2016 | |
| CN | 205072064 U | 3/2016 | |
| CN | 205180371 U | 4/2016 | |
| CN | 205214209 U | 5/2016 | |
| CN | 105722416 A | 6/2016 | |
| CN | 205358219 U | 7/2016 | |
| CN | 205358225 U | 7/2016 | |
| CN | 105852221 A | 8/2016 | |
| CN | 105852225 A | 8/2016 | |
| CN | 205456064 U | 8/2016 | |
| CN | 105919162 A | 9/2016 | |
| CN | 205624474 U | 10/2016 | |
| CN | 106136331 A | 11/2016 | |
| CN | 106163304 A | 11/2016 | |
| CN | 106170215 A | 11/2016 | |
| CN | 205671480 U | 11/2016 | |
| CN | 106231934 A | 12/2016 | |
| CN | 106235419 A | 12/2016 | |
| CN | 205831079 U | 12/2016 | |
| CN | 106418729 A | 2/2017 | |
| CN | 106473232 A | 3/2017 | |
| CN | 106473233 A | 3/2017 | |
| CN | 106490686 A | 3/2017 | |
| CN | 106535680 A | 3/2017 | |
| CN | 106690427 A | 5/2017 | |
| CN | 106723379 A | 5/2017 | |
| CN | 106793834 A | 5/2017 | |
| CN | 206197012 U | 5/2017 | |
| CN | 106912985 A | 7/2017 | |
| CN | 206314585 U | 7/2017 | |
| CN | 106998816 A | 8/2017 | |
| CN | 107105772 A | 8/2017 | |
| CN | 206442590 U | 8/2017 | |
| CN | 206443202 U | 8/2017 | |
| CN | 206443214 U | 8/2017 | |
| CN | 107173850 A | 9/2017 | |
| CN | 107183789 A | 9/2017 | |
| CN | 107205491 A | 9/2017 | |
| CN | 206462413 U | 9/2017 | |
| CN | 107249366 A | 10/2017 | |
| CN | 107278125 A | 10/2017 | |
| CN | 206547882 U | 10/2017 | |
| CN | 107801375 A | 3/2018 | |
| CN | 108013512 A | 5/2018 | |
| CN | 108835715 A * | 11/2018 | |
| CN | 110325058 A | 10/2019 | |
| CN | 110958841 A | 4/2020 | |
| EA | 201290392 A1 | 10/2012 | |
| EA | 201290240 A1 | 12/2012 | |
| EA | 026076 B1 | 2/2017 | |
| EP | 0 438 862 A2 | 7/1991 | |
| EP | 0 917 831 A1 | 5/1999 | |
| EP | 0 822 760 B1 | 6/2003 | |
| EP | 1 947 965 A2 | 7/2008 | |
| EP | 2 201 850 A1 | 6/2010 | |
| EP | 2 316 286 A1 | 5/2011 | |
| EP | 2 327 318 A1 | 6/2011 | |
| EP | 2 340 729 A1 | 7/2011 | |
| EP | 2368449 A1 | 9/2011 | |
| EP | 2 677 273 A1 | 12/2013 | |
| EP | 2 921 065 A1 | 9/2015 | |
| EP | 3104721 A1 | 12/2016 | |
| EP | 3 257 386 B1 | 6/2019 | |
| EP | 3 248 486 B1 | 8/2019 | |
| EP | 3 569 076 A1 | 11/2019 | |
| EP | 3 248 485 B1 | 4/2020 | |
| EP | 3 656 229 A2 | 5/2020 | |
| EP | 2378905 B1 * | 5/2020 | ............... A24D 1/20 |
| GB | 2 301 894 A | 12/1996 | |
| GB | 2514893 A | 12/2014 | |
| JP | 48-63677 U | 8/1973 | |
| JP | 62-15793 A | 1/1987 | |
| JP | 63-68690 U | 5/1988 | |
| JP | 6-73784 U | 10/1994 | |
| JP | 7-72809 A | 3/1995 | |
| JP | 7-184627 A | 7/1995 | |
| JP | 8-122942 A | 5/1996 | |
| JP | 9-75058 A | 3/1997 | |
| JP | 9-161822 A | 6/1997 | |
| JP | 9-228919 A | 9/1997 | |
| JP | 10-37781 A | 2/1998 | |
| JP | 2001-200495 A | 7/2001 | |
| JP | 2002-514910 A | 5/2002 | |
| JP | 2003-527127 A | 9/2003 | |
| JP | 2004-212102 A | 7/2004 | |

(56) References Cited

FOREIGN PATENT DOCUMENTS

| | | |
|---|---|---|
| JP | 2005-199913 A | 7/2005 |
| JP | 2006252897 A | 9/2006 |
| JP | 2006-292620 A | 10/2006 |
| JP | 3898118 B2 | 3/2007 |
| JP | 2007-101639 A | 4/2007 |
| JP | 2010-266425 A | 11/2010 |
| JP | 2012-513750 A | 6/2012 |
| JP | 2013-509160 A | 3/2013 |
| JP | 2013-524835 A | 6/2013 |
| JP | 2014-132560 A | 7/2014 |
| JP | 2014-216287 A | 11/2014 |
| JP | 2014-533513 A | 12/2014 |
| JP | 2015-13192 A | 1/2015 |
| JP | 2015-503916 A | 2/2015 |
| JP | 2015-504669 A | 2/2015 |
| JP | 2015-506170 A | 3/2015 |
| JP | 2015-528307 A | 9/2015 |
| JP | 2016-512033 A | 4/2016 |
| JP | 2016-521552 A | 7/2016 |
| JP | 2017-506901 A | 3/2017 |
| JP | 2017-510270 A | 4/2017 |
| JP | 2017-511123 A | 4/2017 |
| JP | 2017-127300 A | 7/2017 |
| JP | 2017-522876 A | 8/2017 |
| KR | 1999-0081973 A | 11/1999 |
| KR | 20-0203233 Y1 | 11/2000 |
| KR | 10-0304044 B1 | 11/2001 |
| KR | 10-2004-0084899 A | 10/2004 |
| KR | 10-2005-0065896 A | 6/2005 |
| KR | 10-0495099 B1 | 11/2005 |
| KR | 10-2006-0121638 A | 11/2006 |
| KR | 10-0782063 B1 | 12/2007 |
| KR | 10-1012472 B1 | 2/2011 |
| KR | 10-2011-0096548 A | 8/2011 |
| KR | 10-1062248 B1 | 9/2011 |
| KR | 20-2011-0008931 U | 9/2011 |
| KR | 10-2012-0027029 A | 3/2012 |
| KR | 10-2012-0050568 A | 5/2012 |
| KR | 20-0460461 Y1 | 5/2012 |
| KR | 10-1174189 B1 | 8/2012 |
| KR | 10-2012-0101637 A | 9/2012 |
| KR | 10-2012-0102131 A | 9/2012 |
| KR | 10-2012-0104533 A | 9/2012 |
| KR | 10-2012-0115488 A | 10/2012 |
| KR | 20-2012-0007263 U | 10/2012 |
| KR | 20-2012-0008751 U | 12/2012 |
| KR | 10-2013-0031025 A | 3/2013 |
| KR | 10-1239080 B1 | 3/2013 |
| KR | 10-2013-0084789 A | 7/2013 |
| KR | 10-2013-0139276 A | 12/2013 |
| KR | 10-2013-0139298 A | 12/2013 |
| KR | 10-1338073 B1 | 12/2013 |
| KR | 10-2014-0044165 A | 4/2014 |
| KR | 10-2014-0116055 A | 10/2014 |
| KR | 10-2014-0116381 A | 10/2014 |
| KR | 10-2014-0118980 A | 10/2014 |
| KR | 10-2014-0119029 A | 10/2014 |
| KR | 10-2014-0135568 A | 11/2014 |
| KR | 10-1465846 B1 | 11/2014 |
| KR | 10-1480423 B1 | 1/2015 |
| KR | 10-1486294 B1 | 1/2015 |
| KR | 10-2015-0111021 A | 10/2015 |
| KR | 10-2016-0005323 A | 1/2016 |
| KR | 20160009678 A * | 1/2016 |
| KR | 10-2016-0012154 A | 2/2016 |
| KR | 10-2016-0031801 A | 3/2016 |
| KR | 10-2016-0052607 A | 5/2016 |
| KR | 10-1631286 B1 | 6/2016 |
| KR | 10-1635340 B1 | 6/2016 |
| KR | 10-2016-0082570 A | 7/2016 |
| KR | 10-2016-0086118 A | 7/2016 |
| KR | 10-2016-0088163 A | 7/2016 |
| KR | 10-1660214 B1 | 9/2016 |
| KR | 10-1677547 B1 | 11/2016 |
| KR | 10-1679163 B1 | 11/2016 |
| KR | 10-2017-0006282 A | 1/2017 |
| KR | 10-2017-0020807 A | 2/2017 |
| KR | 10-2017-0057535 A | 5/2017 |
| KR | 10-1733448 B1 | 5/2017 |
| KR | 10-2017-0067171 A | 6/2017 |
| KR | 10-2017-0083596 A | 7/2017 |
| KR | 10-2017-0117444 A | 10/2017 |
| KR | 10-2017-0118233 A | 10/2017 |
| KR | 10-2018-0125852 A | 11/2018 |
| KR | 10-2018-0129637 A | 12/2018 |
| KR | 10-2019-0016907 A | 2/2019 |
| RU | 2 132 629 C1 | 7/1999 |
| RU | 2551944 C1 | 6/2015 |
| RU | 2611487 C2 | 2/2017 |
| RU | 2617297 C2 | 4/2017 |
| RU | 2 619 735 C1 | 5/2017 |
| RU | 2015152134 A | 6/2017 |
| WO | 95/27412 A1 | 10/1995 |
| WO | 98/23171 A1 | 6/1998 |
| WO | 2007039794 A2 | 4/2007 |
| WO | 2009/044716 A1 | 4/2009 |
| WO | 2010073122 A1 | 7/2010 |
| WO | 2011/015826 A1 | 2/2011 |
| WO | 2011/050964 A1 | 5/2011 |
| WO | 2011/063970 A1 | 6/2011 |
| WO | 2013/102609 A2 | 7/2013 |
| WO | 2014/102092 A1 | 7/2014 |
| WO | 2014/195679 A2 | 12/2014 |
| WO | 2015/035510 A1 | 3/2015 |
| WO | 2015/070402 A1 | 5/2015 |
| WO | 2015/082560 A1 | 6/2015 |
| WO | 2015/117702 A1 | 8/2015 |
| WO | 2015/150759 A1 | 10/2015 |
| WO | 2015/168828 A1 | 11/2015 |
| WO | 2015/174657 A1 | 11/2015 |
| WO | 2015/177046 A1 | 11/2015 |
| WO | 2015/189388 A1 | 12/2015 |
| WO | 2016/005601 A1 | 1/2016 |
| WO | 2016/009202 A1 | 1/2016 |
| WO | 2016/012795 A1 | 1/2016 |
| WO | 2016/091658 A1 | 6/2016 |
| WO | 2016/096337 A1 | 6/2016 |
| WO | 2016/111633 A1 | 7/2016 |
| WO | 2016/123738 A1 | 8/2016 |
| WO | 2016/127541 A1 | 8/2016 |
| WO | 2016120177 A1 | 8/2016 |
| WO | 2016/138689 A1 | 9/2016 |
| WO | 2016/184978 A1 | 11/2016 |
| WO | 2016/199065 A1 | 12/2016 |
| WO | 2016/199066 A1 | 12/2016 |
| WO | 2016/207407 A1 | 12/2016 |
| WO | 2017/001520 A1 | 1/2017 |
| WO | 2017/001818 A1 | 1/2017 |
| WO | 2017/005471 A1 | 1/2017 |
| WO | 2017/029089 A1 | 2/2017 |
| WO | 2017/077466 A1 | 5/2017 |
| WO | 2017/133056 A1 | 8/2017 |
| WO | 2017/163046 A1 | 9/2017 |
| WO | 2017/182485 A1 | 10/2017 |
| WO | 2017/211600 A1 | 12/2017 |
| WO | 2018/190606 A1 | 10/2018 |
| WO | 2018/191766 A1 | 10/2018 |
| WO | 2019/015343 A1 | 1/2019 |

OTHER PUBLICATIONS

Office Action dated Jan. 24, 2022 in Chinese Application No. 201880030661.5.
Office Action dated Dec. 24, 2021 in Chinese Application No. 201880055847.6.
Office Action dated Dec. 20, 2021 in Chinese Application No. 201880048655.2.
Office Action dated Jan. 4, 2022 in Chinese Application No. 201880048703.8.
Office Action dated Jan. 18, 2022 in Chinese Application No. 201880052857.4.
Office Action dated Jan. 30, 2022 in Chinese Application No. 201880052855.5.

(56) References Cited

OTHER PUBLICATIONS

"PCB Design and Processing", Seping, pp. 32-35, Beijing Institute of Technology Publishing House, Feb. 2017, Feb. 28, 2017 (6 pages total).
Office Action dated Dec. 31, 2021 in Chinese Application No. 201880049189.X.
Office Action dated Aug. 12, 2019 in Korean Application No. 10-2019-0033722.
Office Action dated Jul. 2, 2019 in Korean Application No. 10-2019-0017392.
Office Action dated Jul. 3, 2019 in Korean Application No. 10-2019-0016835.
Office Action dated May 18, 2019 in Korean Application No. 10-2018-0090063.
Office Action dated Oct. 25, 2019 in Korean Application No. 10-2018-0078296.
Office Action dated Oct. 15, 2019 in Korean Application No. 10-2018-0074188.
Office Action dated Oct. 8, 2019 in Korean Application No. 10-2018-0072992.
Office Action dated Oct. 8, 2019 in Korean Application No. 10-2018-0072935.
Office Action dated Sep. 6, 2019 in Korean Application No. 10-2018-0069645.
Office Action dated Jul. 10, 2019 in Korean Application No. 10-2018-0064487.
Office Action dated Jun. 24, 2019 in Korean Application No. 10-2018-0062137.
Office Action dated Jun. 19, 2019 in Korean Application No. 10-2018-0059580.
Office Action dated May 13, 2019 in Korean Application No. 10-2018-0058596.
Office Action dated May 3, 2019 in Korean Application No. 10-2018-0055120.
Office Action dated Dec. 9, 2019 in Korean Application No. 10-2018-0052133.
Office Action dated Dec. 9, 2019 in Korean Application No. 10-2018-0051469.
Office Action dated Dec. 9, 2019 in Korean Application No. 10-2018-0051467.
International Search Report dated Apr. 16, 2019 in International Application No. PCT/KR2018/012899.
International Search Report dated Apr. 26, 2019 in International Application No. PCT/KR2018/012895.
International Search Report dated May 17, 2019 in International Application No. PCT/KR2018/012810.
International Search Report dated May 17, 2019 in International Application No. PCT/KR2018/012809.
International Search Report dated May 17, 2019 in International Application No. PCT/KR2018/012808.
International Search Report dated May 3, 2019 in International Application No. PCT/KR2018/012807.
International Search Report dated May 17, 2019 in International Application No. PCT/KR2018/012776.
International Search Report dated Apr. 3, 2019 in International Application No. PCT/KR2018/012775.
International Search Report dated Apr. 3, 2019 in International Application No. PCT/KR2018/012774.
International Search Report dated Apr. 3, 2019 in International Application No. PCT/KR2018/012773.
International Search Report dated May 20, 2019 in International Application No. PCT/KR2018/012685.
International Search Report dated May 21, 2019 in International Application No. PCT/KR2018/012676.
International Search Report dated Nov. 26, 2018 in International Application No. PCT/KR2018/005767.
International Search Report dated Aug. 28, 2018 in International Application No. PCT/KR2018/005693.
International Search Report dated Nov. 2, 2018 in International Application No. PCT/KR2018/005306.
Communication dated Jul. 27, 2020 by the Russian Patent Office in application No. 2020110821.
Communication dated Jun. 11, 2020 by the Korean Patent Office in application No. 10-2018-0051469.
Extended European Search Report dated Jan. 15, 2021 in European Application No. 18799246.6.
Office Action dated May 25, 2020 in Russian Application No. 2019135871.
Office Action dated Jun. 10, 2020 in Korean Application No. 10-2018-0052137.
Office Action dated Oct. 5, 2020 in Korean Application No. 10-2020-0090577.
Office Action dated Oct. 16, 2020 in Korean Application No. 10-2020-0092553.
Extended European Search Report dated Nov. 16, 2020 in European Application No. 20189002.7.
Office Action dated Dec. 8, 2020 in Russian Application No. 2020113632.
Office Action dated Nov. 25, 2020 in Russian Application No. 2020124810.
Office Action dated Jan. 26, 2021 in Japanese Application No. 2020-502671.
Office Action dated Dec. 22, 2020 in Japanese Application No. 2020-502181.
Office Action dated Dec. 22, 2020 in Japanese Application No. 2020-503856.
Extended European Search Report dated Nov. 13, 2020 in European Application No. 20188970.6.
Office Action dated Nov. 10, 2020 in Japanese Application No. 2020-523671.
Office Action dated Nov. 24, 2020 in Russian Application No. 2020124811.
Communication dated Feb. 24, 2021 by the Japanese Patent Office in application No. 2020-503962.
Communication dated Mar. 23, 2021 by the Japanese Patent Office in application No. 2020-522897.
Communication dated Mar. 2, 2021 by the Japanese Patent Office in application No. 2020-523669.
Communication dated Mar. 30, 2021 by the Japanese Patent Office in application No. 2020-501446.
Communication dated Mar. 16, 2021 by the Japanese Patent Office in application No. 2020-521441.
Communication dated Feb. 9, 2021 by the Japanese Patent Office in application No. 2020-501205.
Communication dated Mar. 16, 2021 by the European Patent Office in application No. 18806877.9.
Extended European Search Report dated Sep. 9, 2021 in European Application No. 18873562.5.
Office Action dated Aug. 3, 2021 in Japanese Application No. 2020-503856.
Extended European Search Report dated Aug. 18, 2021 in European Application No. 18874344.7.
Extended European Search Report dated Jul. 30, 2021 in European Application No. 18874446.0.
Extended European Search Report dated Aug. 17, 2021 in European Application No. 18872432.2.
Office Action dated Aug. 17, 2021 in Japanese Application No. 2020-503962.
Extended European Search Report dated Aug. 10, 2021 in European Application No. 18873846.2.
Extended European Search Report dated Aug. 17, 2021 in European Application No. 18873943.7.
Extended European Search Report dated Aug. 10, 2021 in European Application No. 18874742.2.
Extended European Search Report dated Aug. 12, 2021 in European Application No. 18874837.0.
Extended European Search Report dated Aug. 20, 2021 in European Application No. 18874962.6.
Extended European Search Report dated Aug. 6, 2021 in European Application No. 18872527.9.
Extended European Search Report dated Sep. 2, 2021 in European Application No. 18874839.6.

(56) References Cited

OTHER PUBLICATIONS

Extended European Search Report dated Jul. 20, 2021 in European Application No. 18872006.4.
Office Action dated Sep. 3, 2021 in Chinese Application No. 201880035480.1.
Office Action dated Aug. 11, 2021 in Chinese Application No. 201880029050.9.
Extended European Search Report dated Oct. 15, 2021 in European Application No. 18872138.5.
Communication dated Dec. 3, 2021 from the Chinese Patent Office in Chinese Application No. 201880049465.2.
Communication dated Dec. 2, 2021 from the Chinese Patent Office in Chinese Application No. 201880048657.1.
Communication dated Dec. 2, 2021 from the Chinese Patent Office in Chinese Application No. 201880048444.9.
Office Action dated Apr. 5, 2019 in Korean Application No. 10-2019-0017393.
Office Action dated Apr. 25, 2019 in Korean Application No. 10-2019-0033722.
Office Action dated Apr. 25, 2019 in Korean Application No. 10-2019-0033723.
Office Action dated Jun. 7, 2021 in Canadian Application No. 3,076,886.
Office Action dated Feb. 9, 2018 in Korean Application No. 10-2017-0058786.
Communication dated Feb. 28, 2022 from the Chinese Patent Office in Chinese Application No. 201880063459.2.
Communication dated Mar. 29, 2022 from the Japanese Patent Office in Japanese Application No. 2020-522897.
Communication dated Mar. 3, 2022 from the Chinese Patent Office in Chinese Application No. 201880058682.8.
Wenxue Geng et al., "Technology Manual of a Programmable Controller", Science Technology, 1st Edition, 1996, p. 132 (2 pages total).
Office Action dated Jul. 4, 2022, issued in Chinese Application No. 201880048657.1.
Office Action dated Aug. 26, 2022, issued in Chinese Application No. 201880048703.8.
Office Action dated Jun. 28, 2022, issued in Japanese Application No. 2020-522897.
Office Action dated Jul. 12, 2022, issued in Chinese Application No. 201880049189.X.
Su Zuen et al., "Heat Transfer", Dalian Maritime University Press, Feb. 28, 1989, pp. 12-13 (9 pages total).
Office Action dated Jun. 22, 2022, issued in Chinese Application No. 201880048444.9.
Office Action dated Nov. 1, 2022 from Japanese Patent Office in JP Application No. 2020-501205.
Office Action dated Dec. 29, 2022 from the China National Intellectual Property Administration in CN Application No. 201880055847.6.
Office Action dated Dec. 20, 2022 from the Japanese Patent Office in JP Application No. 2021-122551.
Office Action dated Jan. 10, 2023 from the Japanese Patent Office in JP Application No. 2021-080578.
Office Action dated Jan. 20, 2023 from the China National Intellectual Property Administration in CN Application No. 202010761215.0.
Office Action dated Jan. 28, 2023 from the China National Intellectual Property Administration in CN Application No. 202010761219.9.
Office Action dated Feb. 14, 2023 from the Japanese Patent Office in JP Application No. 2022-074915.
Office Action dated Mar. 30, 2023 in Chinese Application No. 201880030661.5.
Office Action dated May 12, 2023 in Chinese Application No. 201880048703.8.
Wei-Ping Jia et al., "Determination of Aerosol Concentration in Mainstream Cigarette Smoke Based on Online Impact", Tobacco Science & Technology, Manufacturing Technology, Dec. 2010, vol. 281 (4 pages total).
Third Office Action issued in the China National Intellectual Property Administration on Feb. 23, 2024, issued in corresponding CN Patent Application No. 202010761215.0.
Extended European search report dated Dec. 12, 2023 in Application No. 23210344.0.

* cited by examiner

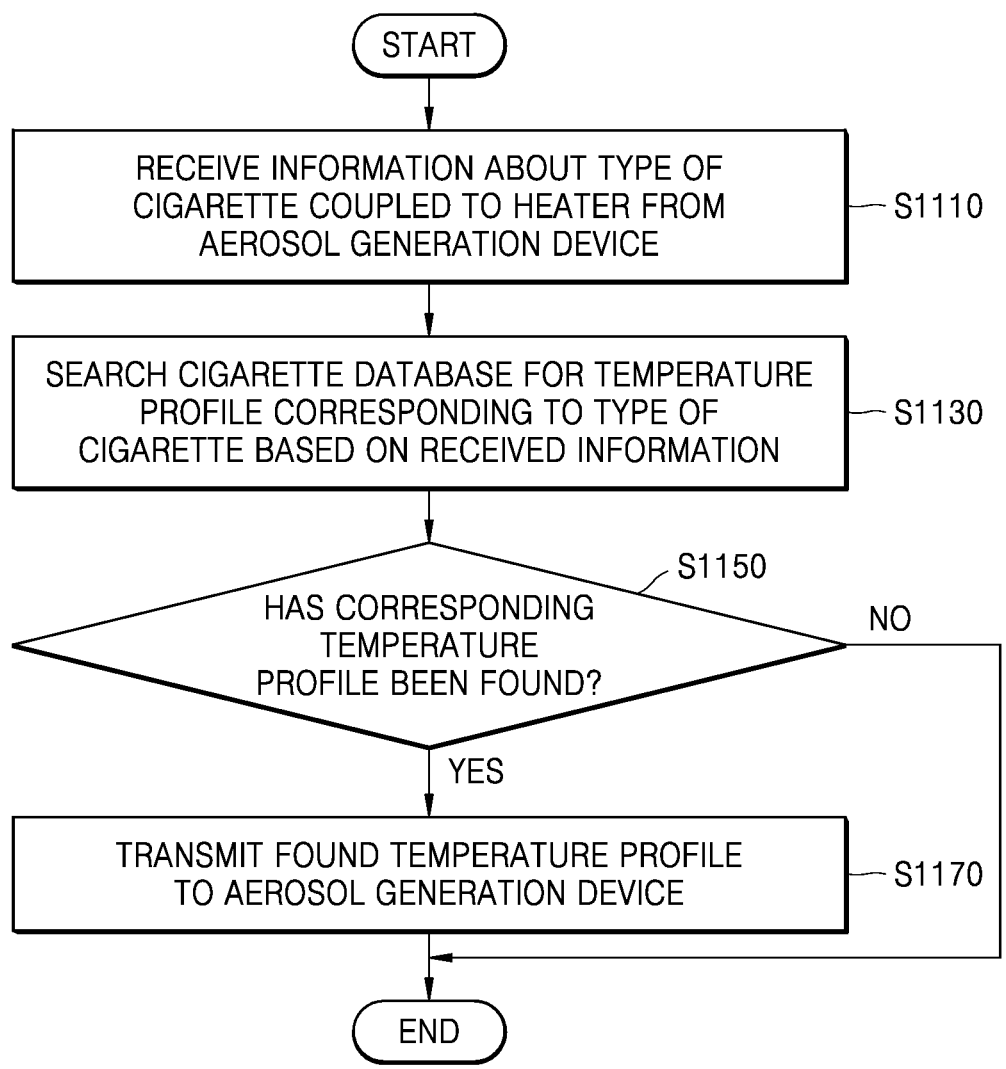

METHOD FOR CONTROLLING TEMPERATURE OF HEATER INCLUDED IN AEROSOL GENERATION DEVICE ACCORDING TO TYPE OF CIGARETTE, AND AEROSOL GENERATION DEVICE FOR CONTROLLING TEMPERATURE OF HEATER ACCORDING TO TYPE OF CIGARETTE

CROSS REFERENCE TO RELATED APPLICATIONS

This application is a National Stage of International Application No. PCT/KR2018/005767, filed May 21, 2018, claiming priorities to Korean Patent Application No. 10-2017-0142578, filed Oct. 30, 2017, Korean Patent Application No. 10-2017-0146972, filed Nov. 6, 2017, Korean Patent Application No. 10-2017-0156729, filed Nov. 22, 2017 and Korean Patent Application No. 10-2018-0052133, filed May 4, 2018.

TECHNICAL FIELD

The present disclosure relates to a method of controlling the temperature of a heater included in an aerosol generation device and an aerosol generation device for controlling the temperature of a heater according to the type of cigarette, and more particularly, to a method of heating a heater based on temperature profiles that are different according to the type of cigarette, which is inserted into an inner space of an aerosol generation device and contacts the heater, and an aerosol generation device for realizing the method.

BACKGROUND ART

Recently, there has been an increasing demand for an alternative method of overcoming the disadvantages of normal cigarettes. For example, instead of a method of generating an aerosol by burning a cigarette, a method of generating an aerosol by heating an aerosol generating material of a cigarette has been increasingly demanded. Therefore, there has been active research into a heating-type cigarette or a heating-type aerosol generation device.

DESCRIPTION OF EXEMPLARY EMBODIMENTS

Technical Problem

Provided are a method of identifying the type of cigarette inserted into an inner space of an aerosol generation device and providing an optimal heating temperature to the identified cigarette and an aerosol generation device for realizing the method.

Solution to Problem

According to an aspect of the present disclosure, a method includes a profile receiving step of receiving temperature profiles according to the type of cigarette from a user terminal; a cigarette sensing step of sensing a cigarette coupled to the heater after receiving the temperature profiles; a profile selecting step of identifying the type of the sensed cigarette and selecting a temperature profile corresponding to the identified type from the temperature profiles; and a power control step of controlling power of a battery according to the selected temperature profile, the power of the battery being supplied to the heater.

According to another aspect of the present disclosure, a method of controlling a temperature of a heater included in an aerosol generation device according to a type of cigarette through communication with a user terminal includes a cigarette sensing step of sensing coupling of a cigarette to the heater; a cigarette identifying step of identifying type information of the cigarette; a profile acquiring step of acquiring a temperature profile corresponding to the type information of the cigarette; and a power control step of controlling the temperature of the heater according to the acquired temperature profile.

According to still another aspect of the present disclosure, an aerosol generation device, which generates an aerosol inhalable by a user when a cigarette is coupled to a heater and power is supplied to the heater, includes a profile receiver configured to receive temperature profiles according to the type of cigarette from a user terminal; a cigarette sensor configured to sense the cigarette coupled to the heater after receiving the temperature profiles; a profile selector configured to identify a type of the cigarette and select a temperature profile corresponding to the type of the cigarette from the temperature profiles; and a power controller configured to control power of a battery according to the temperature profile, the power of the battery being supplied to the heater.

According to a further aspect of the present disclosure, an aerosol generation device, which generates an aerosol inhalable by a user when a cigarette is coupled to a heater and power is supplied to the heater, includes a cigarette sensor configured to sense coupling of the cigarette to the heater; a cigarette identification unit configured to identify type information of the cigarette; a profile acquisition unit configured to acquire a temperature profile according to the type information of the cigarette; and a power controller configured to control the temperature of the heater according to the temperature profile.

An exemplary embodiment of the present disclosure may provide a recording medium having stored therein a program for performing the method.

Advantageous Effects of Disclosure

According to the present disclosure, a user may inhale the aerosol generated by heating a cigarette to an optimal temperature that is preset according to the type of cigarette, thereby having a satisfactory smoking experience.

In addition, a user may manually set a temperature profile to the user's preference in addition to the preset temperature profiles.

BRIEF DESCRIPTION OF DRAWINGS

FIG. 11 is a flowchart of a further example of a method of controlling the temperature of a heater of an aerosol generation device according to the type of cigarette, according to the present disclosure.

BEST MODE

Figure 1:
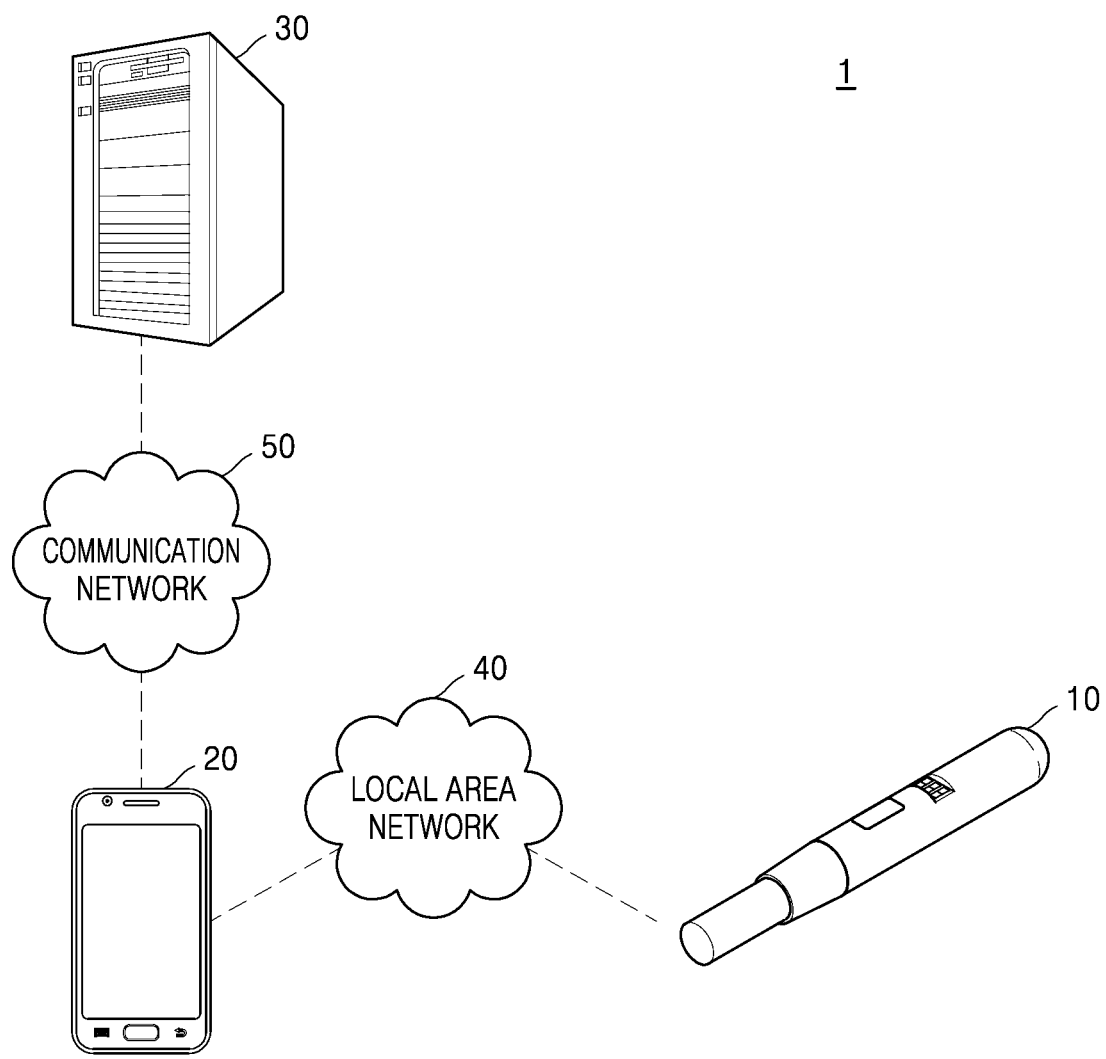
FIG. 1 is a diagram schematically illustrating an example of an entire system according to the present disclosure.

According to an aspect of the present disclosure, a method of controlling a temperature of a heater included in an aerosol generation device according to a type of cigarette includes receiving temperature profiles of different types of cigarette from a user terminal; sensing a cigarette coupled to the heater after receiving the temperature profiles; identifying a type of the sensed cigarette; selecting a temperature profile corresponding to the identified type from among the temperature profiles; and controlling power supplied from a battery to the heater according to the selected temperature profile.

The temperature profiles of different types of cigarette may be received by the user terminal from a cigarette database for storing the temperature profiles according to the type of cigarette.

The temperature profiles of different types of cigarette received from the user terminal may be generated based on information input through an input device of the user terminal.

The information may be input by recognizing one of quick reference (QR) code, bar code, and case code that are attached to a cigarette case.

According to another aspect of the present disclosure, a method of controlling a temperature of a heater included in an aerosol generation device according to a type of cigarette includes sensing coupling of a cigarette to the heater; identifying a type of the cigarette; acquiring a temperature profile corresponding to the type of the cigarette; and controlling the temperature of the heater according to the acquired temperature profile.

The acquiring may include acquiring temperature profiles of different types of cigarette from a storage device for storing the temperature profiles of different types of cigarette.

The acquiring may include acquiring temperature profiles of different types of cigarette from information input by a user.

The acquiring may include transmitting information about the type of the cigarette to a user terminal and receiving the temperature profile corresponding to the information from the user terminal.

The identifying may include identifying the type of the cigarette using a radio frequency identification (RFID) reader sensing an RFID tag attached to the cigarette, and the acquiring includes transmitting information about the type of the cigarette identified using the RFID reader to a user terminal and receiving the temperature profile corresponding to the information from the user terminal.

The sensing may include sensing the coupling of the cigarette to the heater according to a result of recognizing one of QR code, bar code, and an optical sticker that are attached to the cigarette.

The selecting may include identifying the type of the cigarette based on the number of bumps formed on a coupling portion of the cigarette coupled to the heater.

According to still another aspect of the present disclosure, a method of providing a temperature profile of a heater to an aerosol generation device includes receiving information about a type of a cigarette coupled to the heater from the aerosol generation device; searching a cigarette database for a temperature profile corresponding to the type of the cigarette based on the received information; and transmitting the temperature profile found in the cigarette database to the aerosol generation device.

The cigarette database may be included in a user terminal.

The cigarette database may be included in a server connected to a user terminal through a communication network.

According to even another aspect of the present disclosure, a method of controlling a temperature of a heater of an aerosol generation device includes displaying, performed by a user terminal, a plurality of temperature profiles of different types of cigarette through a display unit included in the user terminal; transmitting, performed by the user terminal, at least one temperature profile to the aerosol generation device when the at least one temperature profile is selected based on information received through an input device included in the user terminal; and controlling, performed by the aerosol generation device, the temperature of the heater according to the at least one temperature profile when a cigarette is coupled to the heater of the aerosol generation device.

According to yet another aspect of the present disclosure, a method of controlling a temperature of a heater of an aerosol generation device includes displaying, performed by a user terminal, a plurality of types of cigarette through a display unit included in the user terminal; searching, performed by the user terminal, for a temperature profile corresponding to a type of cigarette determined based on information input through an input device included in the user terminal, in a cigarette database that stores temperature profiles of different types of cigarette; and receiving, performed by the aerosol generation device, the temperature profile and controlling, performed by the aerosol generation device, the temperature of the heater according to the temperature profile when a cigarette is coupled to the heater of the aerosol generation device.

According to a further aspect of the present disclosure, a method of controlling a temperature of a heater of an aerosol generation device includes displaying a plurality of temperature profiles through a display unit included in a user terminal; transmitting at least one temperature profile to the aerosol generation device when the at least one temperature profile is selected based on information input through an input device included in the user terminal; and receiving, performed by the aerosol generation device, the at least one temperature profile and controlling, performed by the aerosol generation device, the temperature of the heater according to the at least one temperature profile when a cigarette is coupled to the heater of the aerosol generation device.

According to a still further aspect of the present disclosure, an aerosol generation device includes a profile receiver configured to receive temperature profiles of different types of cigarette from a user terminal; a cigarette sensor configured to sense a cigarette coupled to a heater after receiving the temperature profiles; a profile selector configured to identify a type of the sensed cigarette and select a temperature profile corresponding to the type of the cigarette from among the temperature profiles; and a power controller configured to control power supplied by a battery to the heater according to the selected temperature profile.

According to an even further aspect of the present disclosure, an aerosol generation device includes a cigarette sensor configured to sense coupling of a cigarette to a heater; a cigarette identification unit configured to identify a type of the sensed cigarette; a profile acquisition unit configured to acquire a temperature profile corresponding to the identified type of the cigarette; and a power controller configured to control a temperature of the heater according to the acquired temperature profile.

An exemplary embodiment of the present disclosure may provide a recording medium having stored therein a program for performing the method.

MODE OF DISCLOSURE

General terms that are now widely used are selected in the description of exemplary embodiments, as far as possible, taking into account functions in the present disclosure, but the terms used herein may be changed according to the intention of one of skill in the art, precedents, the advent of new technology, or the like. There are terms discretionally selected by an applicant on particular occasions. These terms will be explained in detail in relevant description. Therefore, terms used herein are not just names but should be defined based on the meaning of the terms and the whole content of the present disclosure.

In the specification, when a portion "comprises" or "includes" an element, it means that the portion may further comprise or include other elements and does not preclude the presence other elements unless stated otherwise. In addition, terminology such as "part (or unit)" and "module" may indicate a unit which processes at least one function or operation and may be implemented by hardware, software, or a combination thereof.

Exemplary embodiments of the present disclosure will be described in detail hereinafter with reference to the accompanying drawings so as to be easily implemented by one of ordinary skill in the art to which the present disclosure belongs. The present disclosure may, however, be embodied in many different forms and is not limited to the exemplary embodiments set forth herein.

Hereinafter, exemplary embodiments of the present disclosure will be described in detail with reference to the drawings.

FIG. 1 is a diagram schematically illustrating an example of an entire system according to the present disclosure.

Referring to FIG. 1, it may be seen that a system 1, which controls the temperature of a heater included in an aerosol generation device according to the type of cigarette, includes an aerosol generation device 10, a user terminal 20, and a cigarette database 30, which exchange information one another through various communication networks.

The aerosol generation device 10 includes a heater, which is heated by receiving electric power from a power source such as a battery, and a cigarette, which generates an aerosol inhalable by a user. The aerosol generation device 10 includes a communication interface for communication with the user terminal 20 through a local area network 40.

Functions of the aerosol generation device 10 will be described in detail with reference to FIGS. 2 and 3.

The user terminal 20 refers to an electronic device that includes a display unit displaying a screen and an input device receiving data from a user. The input device of the user terminal 20 may include at least one selected from a keyboard, a mouse, a track ball, a microphone, a mechanical button, and a touch panel.

Although the user terminal 20 is illustrated as a smart phone in FIG. 1, the user terminal 20 is not limited to the smart phone and may include any portable terminal such as a tablet personal computer (PC) or a netbook.

The cigarette database 30 is a server that stores many temperature profiles with respect to a cigarette, which generates aerosol when it is inserted into the aerosol generation device 10 and contacts a heater that has heated up. The cigarette database 30 communicates with the user terminal 20 through a communication network. The cigarette database 30 receives a request from the user terminal 20 and transmits a temperature profile to the user terminal 20 according to the type of cigarette.

The local area network 40 connects the aerosol generation device 10 to the user terminal 20. Examples of a local area network protocol used in exemplary embodiments include near field communication (NFC) having a working distance of about 10 cm, Bluetooth having a working distance of about 10 m, and Wi-Fi Direct having a working distance of about several tens of meters.

Local area communication generically refers to processes in which the aerosol generation device 10 and the user terminal 20 set a session with unique identification code and exchange various kinds of information according to the session. In the state where one of the local area communication functions of the aerosol generation device 10 and a corresponding local area communication function of the user terminal 20 are activated, when the user terminal 20 accepts a local area communication setting request of the aerosol generation device 10, communication between the aerosol generation device 10 and the user terminal 20 is made possible without involvement of a separate service provider's server. According to exemplary embodiments, the session between the aerosol generation device 10 and the user terminal 20 may be set in the reverse order of what is described above.

A communication network 50 may connect the user terminal 20 to the cigarette database 30 and may include various wireless communication networks such as a data network, a mobile communication network, and the Internet.

Figure 2:
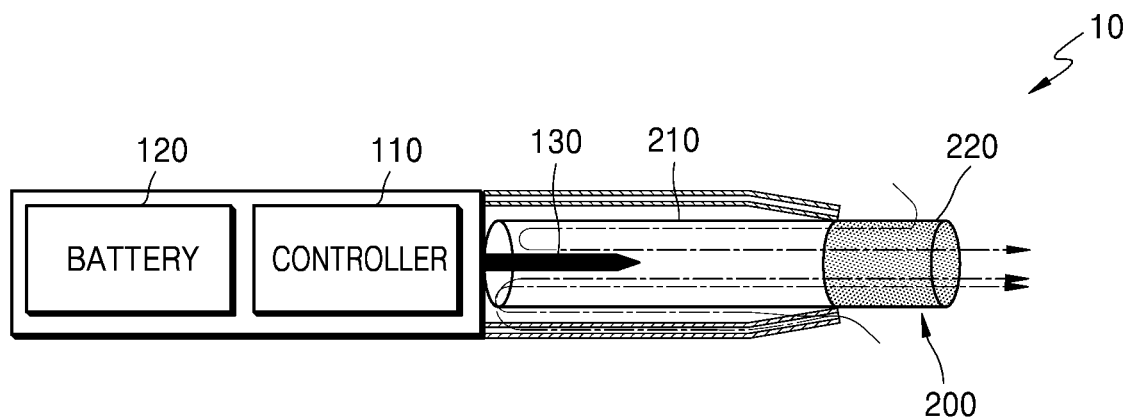
FIG. 2 is a diagram of an example in which a cigarette is inserted into an aerosol generation device.

FIG. 2 is a diagram showing example in which a cigarette is inserted into an aerosol generating device.

Referring to FIG. 2, the aerosol generating device 10 may include a battery 120, a controller 110, and a heater 130. Also, the cigarette 200 may be inserted into an inner space of the aerosol generating device 10

FIG. 2 illustrate components of the aerosol generating device 10, which are related to the present exemplary embodiment. Therefore, it will be understood by one of ordinary skill in the art related to the present exemplary embodiment that other general-purpose components may be further included in the aerosol generating device 10, in addition to the components illustrated in FIG. 2.

FIG. 2 illustrates that the battery 120, the controller 110, and the heater 1300 are arranged in series. In other words, according to the design of the aerosol generating device 10, the battery 120, the controller 110 and the heater 130 may be differently arranged.

When the cigarette 200 is inserted into the aerosol generating device 10, the aerosol generating device 10 may operate the heater 130 to generate an aerosol from the cigarette 200. The generated aerosol is delivered to a user after passing through the filter of the cigarette 200.

As necessary, even when the cigarette 200 is not inserted into the aerosol generating device 10, the aerosol generating device 10 may heat the heater 130.

The battery 120 may supply power to be used for the aerosol generating device 10 to operate. For example, the battery 120 may supply power to heat the heater 130 or the vaporizer 180, and may supply power for operating the controller 110. Also, the battery 120 may supply power for operations of a display, a sensor, a motor, etc. mounted in the aerosol generating device 10.

The controller 110 may generally control operations of the aerosol generating device 10. In detail, the controller 110 may control not only operations of the battery 120 and the heater 130 but also operations of other components included in the aerosol generating device 10. Also, the controller 110 may check a state of each of the components of the aerosol generating device 10 to determine whether or not the aerosol generating device 10 is in an operable state.

The controller 110 may include at least one processor. A processor can be implemented as an array of a plurality of logic gates or can be implemented as a combination of a general-purpose microprocessor and a memory in which a program executable in the microprocessor is stored. It will be understood by one of ordinary skill in the art that the processor can be implemented in other forms of hardware.

The heater 130 may be heated by the power supplied from the battery 120. For example, when the cigarette 200 is inserted into the aerosol generating device 10, the heater 130 may be located outside the cigarette 200. Thus, the heated heater 130 may increase a temperature of an aerosol generating material in the cigarette 200.

The heater 130 may include an electro-resistive heater. For example, the heater 130 may include an electrically conductive track, and the heater 130 may be heated when currents flow through the electrically conductive track. However, the heater 130 is not limited to the example described above and may include any other heather that is capable of being heated to a desired temperature. Here, the desired temperature may be pre-set in the aerosol generating device 10 or may be set manually by a user.

As another example, the heater 130 may include an induction heater. In detail, the heater 130 may include an electrically conductive coil for heating a cigarette in an induction heating method, and the cigarette may include a susceptor which may be heated by the induction heater.

FIG. 2 shows that the heater 130 is arranged to be inserted into the cigarette 200, but the arrangement of the heater 130 is not limited thereto. For example, the heater 130 may include a tube-type heating element, a plate-type heating element, a needle-type heating element, or a rod-type heating element, and may heat the inside or the outside of the cigarette 200, according to the shape of the heating element.

Also, the aerosol generating device 10 may include a plurality of heaters 130. Here, the plurality of heaters 130 may be inserted into the cigarette 200 or may be arranged outside the cigarette 200. Also, some of the plurality of heaters 130 may be inserted into the cigarette 200 and the others may be arranged outside the cigarette 200. In addition, the shape of the heater 130 is not limited to the shapes illustrated in FIG. 2 and the heater 130 may be manufactured in various shapes.

The aerosol generating device 10 may further include general-purpose components in addition to the battery 120, the controller 110 and the heater 130. For example, the aerosol generating device 10 may include a display capable of outputting visual information and/or a motor for outputting haptic information. Also, the aerosol generating device 10 may include at least one sensor (a puff detecting sensor, a temperature detecting sensor, a cigarette insertion detecting sensor, etc.). Also, the aerosol generating device 10 may have a structure that allows external air may be introduced or internal air may be discharged, while the cigarette 200 is inserted into the aerosol generating device 10.

Although not illustrated in FIG. 2, the aerosol generating device 10 and an additional cradle may form a system. For example, the cradle may be used to charge the battery 120 of the aerosol generating device 10. Alternatively, the heater 130 may be heated when the cradle and the aerosol generating device 10 are coupled to each other.

The cigarette 200 may be similar to a general combustive cigarette. For example, the cigarette 200 may be divided into a first portion 210 including an aerosol generating material and a second portion including a filter, etc. Alternatively, the second portion of the cigarette 200 may also include an aerosol generating material. For example, an aerosol generating material made in the form of granules or capsules may be inserted into the second portion.

The entire first portion may be inserted into the aerosol generating device 10, and the second portion may be exposed to the outside. Alternatively, the first portion may be partially inserted into the aerosol generating device 10. Otherwise, the entire first portion and a part of the second portion may be inserted into the aerosol generating device 10. The user may puff aerosol while holding the second portion by the mouth of the user. In this case, the aerosol is generated by the external air passing through the first portion, and the generated aerosol passes through the second portion and is delivered to the user's mouth.

For example, the external air may flow into at least one air passage formed in the aerosol generating device 10. For example, opening and closing of the air passage and/or a size of the air passage may be adjusted by the user. Accordingly, the amount of smoke and a smoking impression may be adjusted by the user. As another example, the external air may flow into the cigarette 200 through at least one hole formed in a surface of the cigarette 200.

Hereinafter, an example of the cigarette 200 will be described with reference to FIG. 3.

Figure 3:
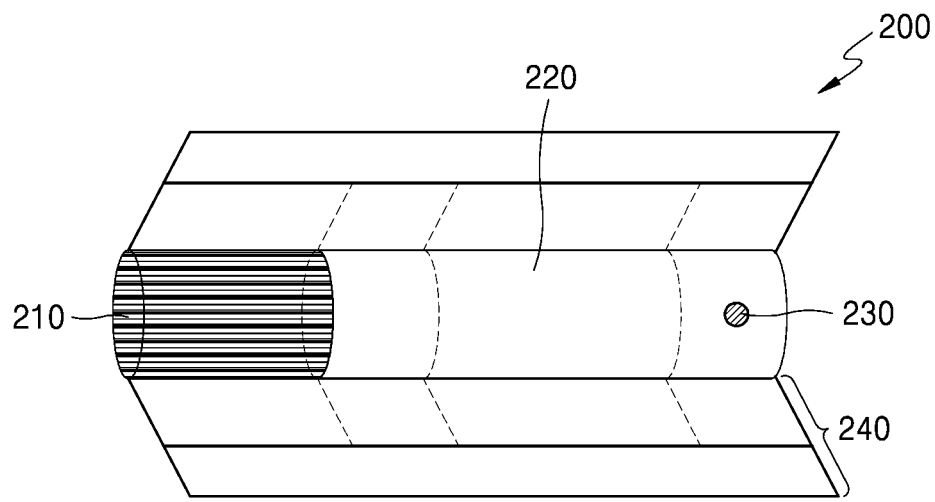
FIG. 3 is a diagram of an example of a cigarette.

FIG. 3 illustrates an example of a cigarette.

Referring to FIG. 3, the cigarette 200 may include a tobacco rod 210 and a filter rod 220. The first portion 210 described above with reference to FIG. 2 may include the tobacco rod, and the second portion may include the filter rod 220.

FIG. 3 illustrates that the filter rod 220 includes a single segment. However, the filter rod 220 is not limited thereto. In other words, the filter rod 220 may include a plurality of segments. For example, the filter rod 220 may include a first segment configured to cool aerosol and a second segment configured to filter a certain component included in the aerosol. Also, as necessary, the filter rod 220 may further include at least one segment configured to perform other functions.

The cigarette 200 may be packaged using at least one wrapper 240. The wrapper 240 may have at least one hole through which external air may be introduced or internal air may be discharged. For example, the cigarette 200 may be packaged using one wrapper 240. As another example, the cigarette 200 may be doubly packaged using at least two wrappers 240. For example, the tobacco rod 210 may be packaged using a first wrapper, and the filter rod 220 may be packaged using a second wrapper. Also, the tobacco rod 210 and the filter rod 220, which are respectively packaged using separate wrappers, may be coupled to each other, and the entire cigarette 200 may be packaged using a third wrapper. When each of the tobacco rod 210 and the filter rod 220 includes a plurality of segments, each segment may be packaged using a separate wrapper. Also, the entire cigarette 200 including the plurality of segments, which are respectively packaged using the separate wrappers and which are coupled to each other, may be re-packaged using another wrapper.

The tobacco rod 210 may include an aerosol generating material. For example, the aerosol generating material may include at least one of glycerin, propylene glycol, ethylene glycol, dipropylene glycol, diethylene glycol, triethylene glycol, tetraethylene glycol, and oleyl alcohol, but it is not limited thereto. Also, the tobacco rod 210 may include other additives, such as flavors, a wetting agent, and/or organic acid. Also, the tobacco rod 210 may include a flavored liquid, such as menthol or a moisturizer, which is injected to the tobacco rod 210.

The tobacco rod 210 may be manufactured in various forms. For example, the tobacco rod 210 may be formed as a sheet or a strand. Also, the tobacco rod 210 may be formed as a pipe tobacco, which is formed of tiny bits cut from a tobacco sheet. Also, the tobacco rod 210 may be surrounded by a heat conductive material. For example, the heat-conducting material may be, but is not limited to, a metal foil such as aluminum foil. For example, the heat conductive material surrounding the tobacco rod 210 may uniformly distribute heat transmitted to the tobacco rod 210, and thus, the heat conductivity applied to the tobacco rod may be increased and taste of the tobacco may be improved. Also, the heat conductive material surrounding the tobacco rod 210 may function as a susceptor heated by the induction heater. Here, although not illustrated in the drawings, the tobacco rod 210 may further include an additional susceptor, in addition to the heat conductive material surrounding the tobacco rod 210.

The filter rod 220 may include a cellulose acetate filter. Shapes of the filter rod 220 are not limited. For example, the filter rod 220 may include a cylinder-type rod or a tube-type rod having a hollow inside. Also, the filter rod 220 may include a recess-type rod. When the filter rod 220 includes a plurality of segments, at least one of the plurality of segments may have a different shape.

The filter rod 220 may be formed to generate flavors. For example, a flavoring liquid may be injected onto the filter rod 220, or an additional fiber coated with a flavoring liquid may be inserted into the filter rod 220.

Also, the filter rod 220 may include at least one capsule 230. Here, the capsule 230 may generate a flavor or an aerosol. For example, the capsule 230 may have a configuration in which a liquid containing a flavoring material is wrapped with a film. For example, the capsule 230 may have a spherical or cylindrical shape, but is not limited thereto.

When the filter rod 220 includes a segment configured to cool the aerosol, the cooling segment may include a polymer material or a biodegradable polymer material. For example, the cooling segment may include pure polylactic acid alone, but the material for forming the cooling segment is not limited thereto. In some exemplary embodiments, the cooling segment may include a cellulose acetate filter having a plurality of holes. However, the cooling segment is not limited to the above-described example and any other cooling segment that is capable of cooling the aerosol may be used.

Figure 4:
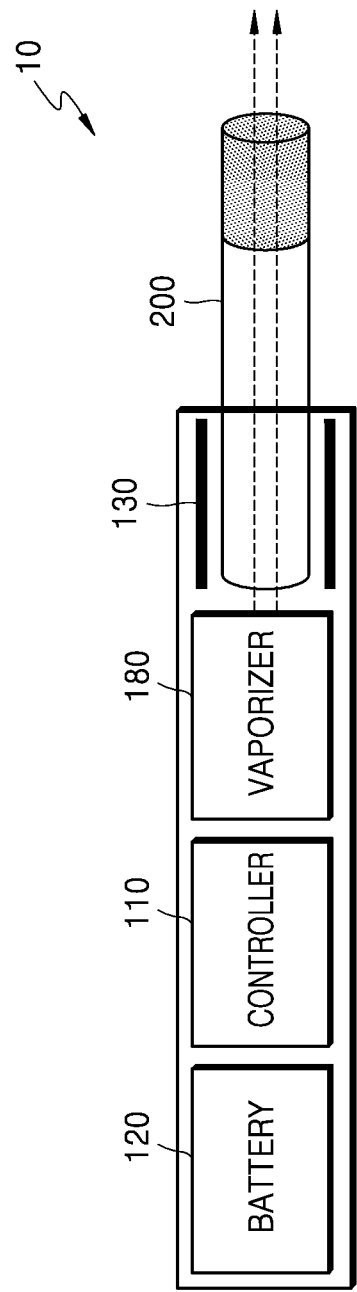
FIG. 4 is a diagram of another example in which a cigarette is inserted into an aerosol generation device.

FIG. 4 illustrates that a cigarette is inserted into an aerosol generating device, according to an exemplary embodiment.

Figure 5:
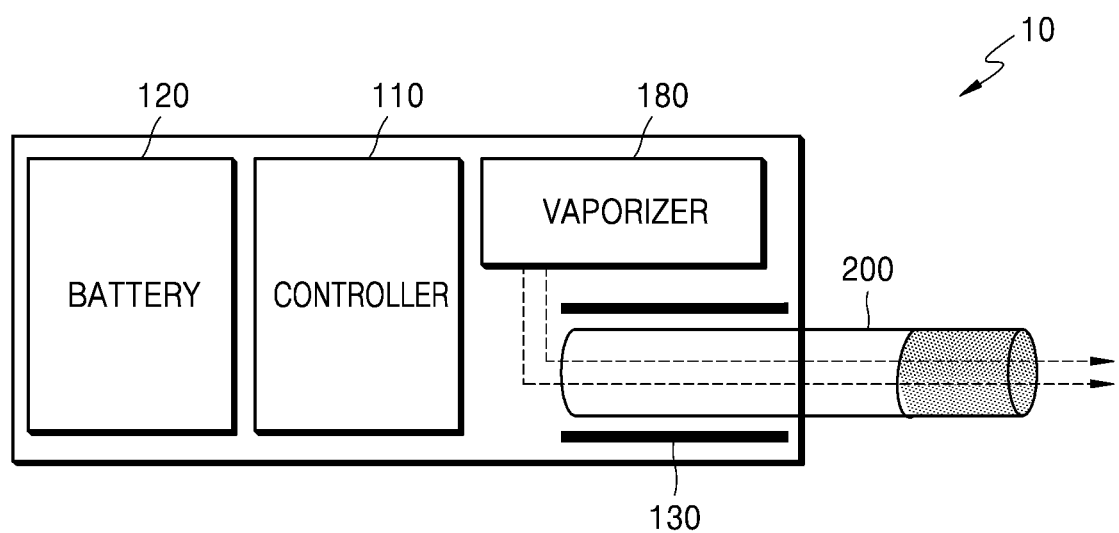
FIG. 5 is a diagram of a further example in which a cigarette is inserted into an aerosol generation device.

FIG. 5 illustrates that a cigarette is inserted into an aerosol generating device, according to another exemplary embodiment.

FIG. 4 illustrates that the battery 120, the controller 110, the vaporizer 180, and the heater 130 are arranged in series, while FIG. 5 illustrates that the vaporizer 180 and the heater 130 are arranged in parallel. However, the internal structure of the aerosol generating device 10 is not limited to the structures illustrated in FIGS. 4 and 5. In other words, according to the design of the aerosol generating device 10, the battery 120, the controller 110, the heater 130, and the vaporizer 180 may be differently arranged.

When the cigarette 200 is inserted into the aerosol generating device 10, the aerosol generating device 10 may operate the heater 130 and/or the vaporizer 180, thereby generating aerosol from the cigarette 200 and/or the vaporizer 180. The aerosol generated by the heater 130 and/or the vaporizer 180 is delivered to a user by passing through the cigarette 200.

Also, the aerosol generating device 10 may include a plurality of heaters 130. Here, the plurality of heaters 130 may be inserted into the cigarette 200 or may be arranged outside the cigarette 200. Also, some of the plurality of heaters 130 may be inserted into the cigarette 200 and the others may be arranged outside the cigarette 200. In addition, the shape of the heater 130 is not limited to the shapes illustrated in FIGS. 4 and 5 and the heater 130 may have various shapes.

The vaporizer 180 may generate aerosol by heating a liquid composition and the generated aerosol may pass through the cigarette 200 to be delivered to a user. In other words, the aerosol generated via the vaporizer 180 may move along an air flow passage of the aerosol generating device 10 and the air flow passage may be configured such that the aerosol generated via the vaporizer 180 passes through the cigarette 200 to be delivered to the user.

For example, the vaporizer 180 may include a liquid storage, a liquid delivery element, and a heating element, but it is not limited thereto. For example, the liquid storage, the liquid delivery element, and the heating element may be included in the aerosol generating device 10 as independent modules.

The liquid storage may store a liquid composition. For example, the liquid composition may be a liquid including a tobacco-containing material having a volatile tobacco flavor component, or a liquid including a non-tobacco material. The liquid storage may be detachable from the vaporizer 180 or may be formed integrally with the vaporizer 180.

For example, the liquid composition may include water, a solvent, ethanol, plant extract, spices, flavorings, or a vitamin mixture. The spices may include menthol, peppermint, spearmint oil, and various fruit-flavored ingredients, but are not limited thereto. The flavorings may include ingredients capable of providing various flavors or tastes to a user. Vitamin mixtures may be a mixture of at least one of vitamin A, vitamin B, vitamin C, and vitamin E, but are not limited thereto. Also, the liquid composition may include an aerosol forming substance, such as glycerin and propylene glycol.

The liquid delivery element may deliver the liquid composition of the liquid storage to the heating element. For example, the liquid delivery element may be a wick such as cotton fiber, ceramic fiber, glass fiber, or porous ceramic, but is not limited thereto.

The heating element is an element for heating the liquid composition delivered by the liquid delivery element. For example, the heating element may be a metal heating wire, a metal hot plate, a ceramic heater, or the like, but is not limited thereto. In addition, the heating element may include a conductive filament such as nichrome wire and may be wound around the liquid delivery element. The heating element may be heated by a current and may transfer heat to the liquid composition in contact with the heating element, thereby heating the liquid composition. As a result, aerosol may be generated.

For example, the vaporizer 180 may be referred to as a cartomizer or an atomizer, but it is not limited thereto.

Figure 6:
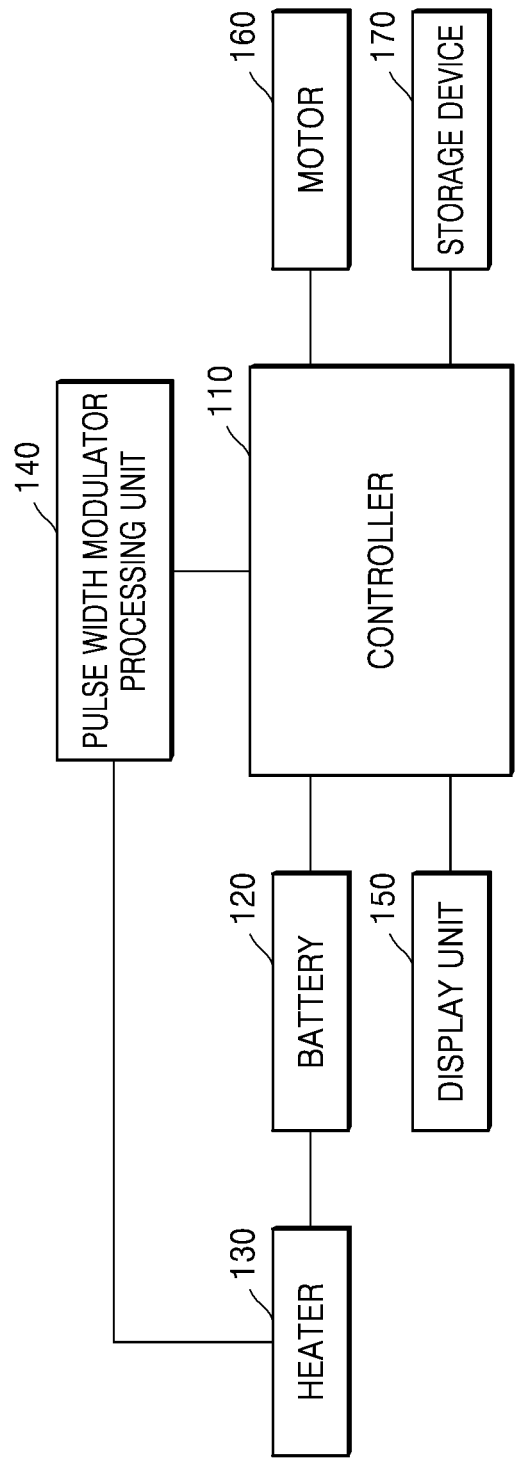
FIG. 6 is a block diagram schematically illustrating an example of an aerosol generation device according to the present disclosure.

FIG. 6 is a block diagram schematically illustrating an aerosol generation device according to an exemplary embodiment.

Referring to FIG. 6, the aerosol generation device 10 includes a controller 110, a battery 120, a heater 130, a pulse width modulator processing unit 140, a display unit 150, a motor 160, and a storage device 170.

The controller 110 controls the battery 120, the heater 130, the pulse width modulator processing unit 140, the display unit 150, the motor 160, and the storage device 170, which are included in the aerosol generation device 10. The controller 110 may include an input receiver (not shown) for receiving a user's button or touch input, and a communicator (not shown) for communicating with an external communication device such as a user terminal, which will be described with reference to FIGS. 7 and 8.

The battery 120 supplies power to the heater 130. The level of power supplied to the heater 130 may be controlled by the controller 110.

When a current is supplied to the heater 130, the heater 130 heats up due to specific resistance. When a cigarette contacts (or is coupled to) the heater 130 that is heated, the aerosol may be generated.

The pulse width modulator processing unit 140 enables the controller 110 to control the power supplied to the heater 130 by transmitting a pulse width modulation (PWM) signal to the heater 130.

The display unit 150 displays to allow a user to select the type of cigarette inserted into an inner space of the aerosol generation device 10 and/or a temperature profile (a temperature control profile) according to the type of cigarette.

The motor 160 is driven by the controller 110 and allows a user to recognize that the aerosol generation device 10 is ready for use.

The storage device 170 stores temperature profiles. The controller 110 fittingly controls the power supplied to the heater 130 based on the temperature profiles to provide various tastes to a user of the aerosol generation device 10. The controller 110 reads at least one temperature profile from the storage device 170 and controls the power supplied to the heater 130 according to the temperature profile. According to the power supplied to the heater 130, the aerosol generated by heating the heater 130 may have different tastes. For example, when a user enjoys smoking using the aerosol generation device 10, the user may feel a soft smoking sensation or a full smoking sensation according to a temperature profile.

Figure 7:
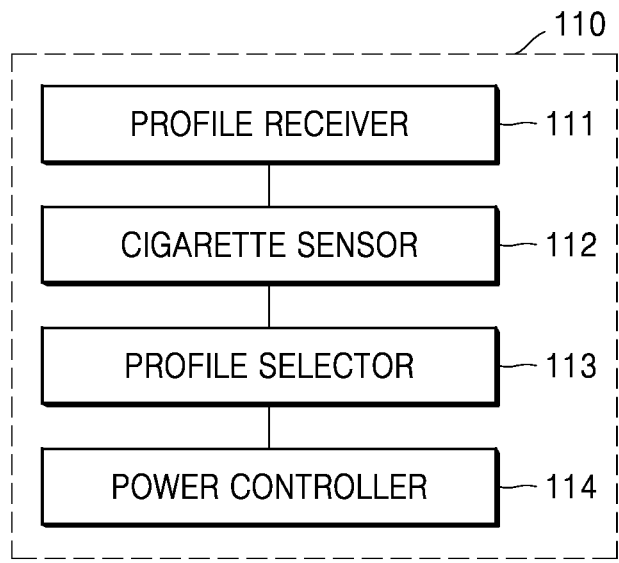
FIG. 7 is a block diagram of an example of a controller included in an aerosol generation device, according to the present disclosure.

FIG. 7 is a block diagram of an example of a controller included in an aerosol generation device, according to the present disclosure.

Referring to FIG. 7, the controller 110 of an aerosol generation device according to an exemplary embodiment may include a profile receiver 111, a cigarette sensor 112, a profile selector 113, and a power controller 114. The controller 110 of FIG. 7 is an example of the controller 110 in FIG. 6. Repetitive description in view of those provided above with reference to FIG. 6 will be omitted.

The profile receiver 111 receives temperature profiles for different types of cigarette from a user terminal. The temperature profiles assigns a different temperature profile to each type of cigarette. The controller 110 may control power supplied to a heater based on the temperature profiles according to the type of cigarette.

For example, when a temperature profile of a cigarette having identification code A is X ° C., the controller 110 controls the temperature of a heater to be X ° C. when cigarette A is inserted into the inner space of the aerosol generation device. Since the temperature profile is set for each type of cigarette, the temperature profile of a cigarette having identification code B may be not X ° C. but Y ° C. Characters A, B, X, and Y are just used for description, and random characters or numerals may be used according to exemplary embodiments.

Even the same type of cigarettes may provide aerosol having different tastes according to the temperature of a heater. Thus, the temperature profiles according to the type of cigarette include temperatures that are experimentally acquired as temperatures giving the best taste to an aerosol of each type of cigarette and may include not only a fixed temperature value but also a variable value changing over time.

In an exemplary embodiment, a user terminal may receive the temperature profiles according to the type of cigarette from a cigarette database. Referring to FIG. 1, the user terminal 20 may communicate various kinds of information with the cigarette database 30 through the communication network 50 and may receive, from the cigarette database 30, a temperature profile of a cigarette inserted into the aerosol generation device 10.

In another exemplary embodiment, the temperature profiles according to the type of cigarette may be generated based on information input through an input device of a user terminal. According to the present optional exemplary embodiment, a user may directly select a temperature profile for a certain cigarette through the input device, such as a soft button, a hard button, or a touch panel, of the user terminal, and an aerosol generation device may generate aerosol according to the temperature profile that has been directly set in this way. The user may directly set a temperature profile most fitting for him or her through the user terminal.

In another exemplary embodiment, a user may enable a user terminal to acquire the temperature profiles according to the type of cigarette by inputting quick reference (QR) code, bar code, or case code, which is attached to a cigarette case, to an input device of the user terminal. When the code attached to the cigarette case is recognized through a smart application installed in the user terminal, the type of cigarette may be identified, and the user terminal may acquire the temperature profiles according to the type of cigarette, which is included in the smart application. In addition, the user terminal may access a cigarette database based on the recognized code and acquire the temperature profiles according to the type of cigarette. In this process, the temperature profiles according to the type of cigarette are transmitted from the user terminal to the profile receiver 111.

The cigarette sensor 112 receives the temperature profile and then senses a cigarette coupled to a heater. Here, the coupling between the heater and the cigarette includes a caser where the distance between the heater and the cigarette is less than a predetermined distance so that identification code on the cigarette may be satisfactorily recognized by the aerosol generation device, as well as a case where the cigarette is in physical contact with the heater.

For example, the cigarette sensor 112 may sense that a cigarette has been coupled to the heater according to a result of recognizing QR code, bar code, or an optical sticker, which is attached to the cigarette.

In another example, the cigarette sensor 112 may identify the type of cigarette based on the number of bumps in a coupling portion of the cigarette coupled to the heater. The cigarette sensor 112 may sense a cigarette as cigarette A when two bumps are recognized and as cigarette B when three bumps are recognized.

In a further example, the cigarette sensor 112 may operate as a radio frequency identification (RFID) reader so as to recognize an RFID tag attached to a cigarette and sense the coupling of the cigarette to the heater.

The profile selector 113 identifies the type of cigarette sensed by the cigarette sensor 112 and selects a temperature profile corresponding to the identified type of cigarette from temperature profiles. The profile selector 113 selects only the temperature profile corresponding to the cigarette sensed by the cigarette sensor 112 from among the temperature profiles received from a user terminal.

The power controller 114 controls the power of a battery, which is supplied to a heater, according to the temperature profile selected by the profile selector 113. In detail, as described above with reference to FIG. 6, the power controller 114 controls a pulse width modulator processing unit based on the temperature profile such that a PWM signal is appropriately provided to the heater.

Figure 8:
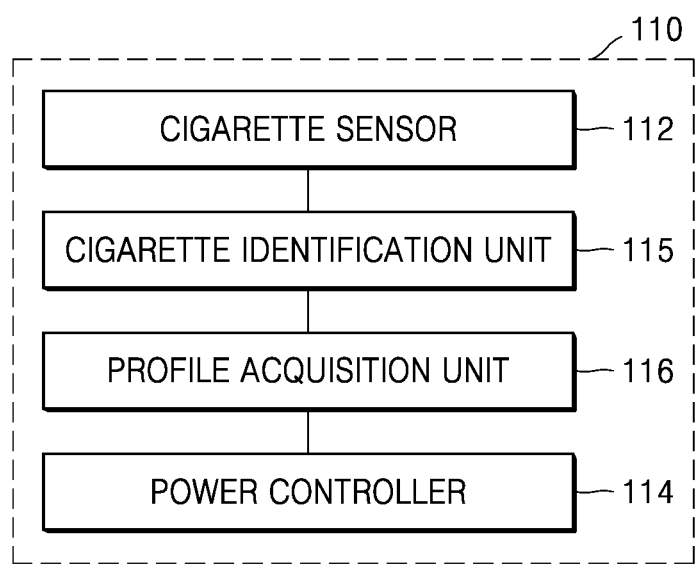
FIG. 8 is a block diagram of another example of a controller included in an aerosol generation device, according to the present disclosure.

FIG. 8 is a block diagram of another example of a controller included in an aerosol generation device, according to the present disclosure.

Referring to FIG. 8, the controller 110 of an aerosol generation device according to another exemplary embodiment may include the cigarette sensor 112, a cigarette identification unit 115, a profile acquisition unit 116, and the power controller 114. The cigarette sensor 112 and the power controller 114 in FIG. 8 are the same as those in FIG. 7. Although not shown, the controller 110 of FIG. 8 may include the profile receiver 111 and the profile selector 113, which have been described with reference to FIG. 7.

The cigarette sensor 112 senses the coupling of a cigarette to a heater. The method by which the cigarette sensor 112 senses the coupling of a cigarette to the heater has been described with reference to FIG. 7.

The cigarette identification unit 115 identifies a type of the cigarette sensed by the cigarette sensor 112. When the cigarette sensor 112 senses that a cigarette contacts the heater and is ready to generate aerosol, the cigarette identification unit 115 identifies the type of the cigarette contacting the heater.

The profile acquisition unit 116 acquires a temperature profile according to the type of the cigarette.

For example, the profile acquisition unit 116 may acquire the temperature profile corresponding to the type of the cigarette from a storage device that stores temperature profiles of different types of cigarette. Here, the storage device that stores the temperature profiles of different types of cigarette may be a memory included in the aerosol generation device, such as the storage device 170 in FIG. 6.

In another example, the profile acquisition unit 116 may acquire the temperature profile based on information input by a user. When the user selects a certain temperature profile through an input device of a user terminal, the selected temperature profile may be transmitted from the user terminal to the profile acquisition unit 116. Alternatively, a user may generate a temperature profile by manually inputting data through an input device of the aerosol generation device.

In another example, the profile acquisition unit 116 may transmit information about the type of the cigarette, which has been identified by the cigarette identification unit 115, to a user terminal and may receive a temperature profile corresponding to the type of the cigarette from the user terminal.

The power controller 114 controls the temperature of the heater according to the temperature profile acquired by the profile acquisition unit 116. A method by which the power controller 114 in FIG. 8 controls the temperature of the heater is the same as that described with reference to FIG. 7.

In the exemplary embodiment described with reference to FIG. 7, the temperature profiles of different types of cigarette are received first and, when the coupling of a cigarette to the heater is sensed, a temperature profile corresponding to the type of the cigarette is selected from the received temperature profiles and the temperature of the heater is controlled. Differently, in the exemplary embodiment described with reference to FIG. 8, the coupling of a cigarette to the heater is sensed and type information of the cigarette is identified, and then a temperature profile is acquired according to the type information of the cigarette.

In an exemplary embodiment, the temperature of a heater of the aerosol generation device 10 may be controlled by a single system including the aerosol generation device 10 and the user terminal 20 in FIG. 1. Firstly, the user terminal 20 displays a plurality of temperature profiles of different types of cigarette through a display unit included therein. A user selects at least one of the temperature profiles through an input device included in the user terminal 20. The selected temperature profile is transmitted to the aerosol generation device 10 and is stored in a storage device of the aerosol generation device 10. Thereafter, when a cigarette is coupled to the heater of the aerosol generation device 10, the aerosol generation device 10 controls the temperature of the heater based on the temperature profile stored in the storage device. According to the present exemplary embodiment, a user selects, according to his or her preference, at least one temperature profile from a plurality of temperature profiles displayed on the user terminal 20, and when a selected cigarette is inserted into the aerosol generation device 10, the temperature of the heater is controlled based on a temperature profile corresponding to the cigarette.

In another exemplary embodiment, the temperature of a heater of the aerosol generation device 10 in FIG. 1 may be controlled according to the type of cigarette, which is selected by a user. Firstly, the user terminal 20 displays a plurality of types of cigarette through a display unit included therein. A user may select a type of cigarette through an input device included in the user terminal 20. When the type of cigarette is determined by the user's input, the user terminal 20 searches for a temperature profile corresponding to the determined type of cigarette in a cigarette database that stores temperature profiles of different types of cigarette, and transmits the temperature profile to the aerosol generation device 10 through the local area network 40. The aerosol generation device 10 receives the temperature profile and controls the temperature of the heater according to the temperature profile when a cigarette is coupled to the heater.

The present exemplary embodiment is different from the previous exemplary embodiment, in which the temperature of the heater of the aerosol generation device 10 is controlled by selecting the temperature profile according to the type of cigarette, in that a user just selects the type of cigarette displayed on the user terminal 20.

In another exemplary embodiment, the temperature of a heater of the aerosol generation device 10 in FIG. 1 may be controlled according to a temperature profile selected by a user regardless of the type of cigarette. In the present exemplary embodiment, the user selects one of the temperature profiles displayed on the user terminal 20, and the temperature of the heater of the aerosol generation device 10 is controlled according to the temperature profile selected by the user, regardless of the type of a cigarette coupled to the heater. Accordingly, the temperature of the heater may be controlled with consistency.

Figure 9:
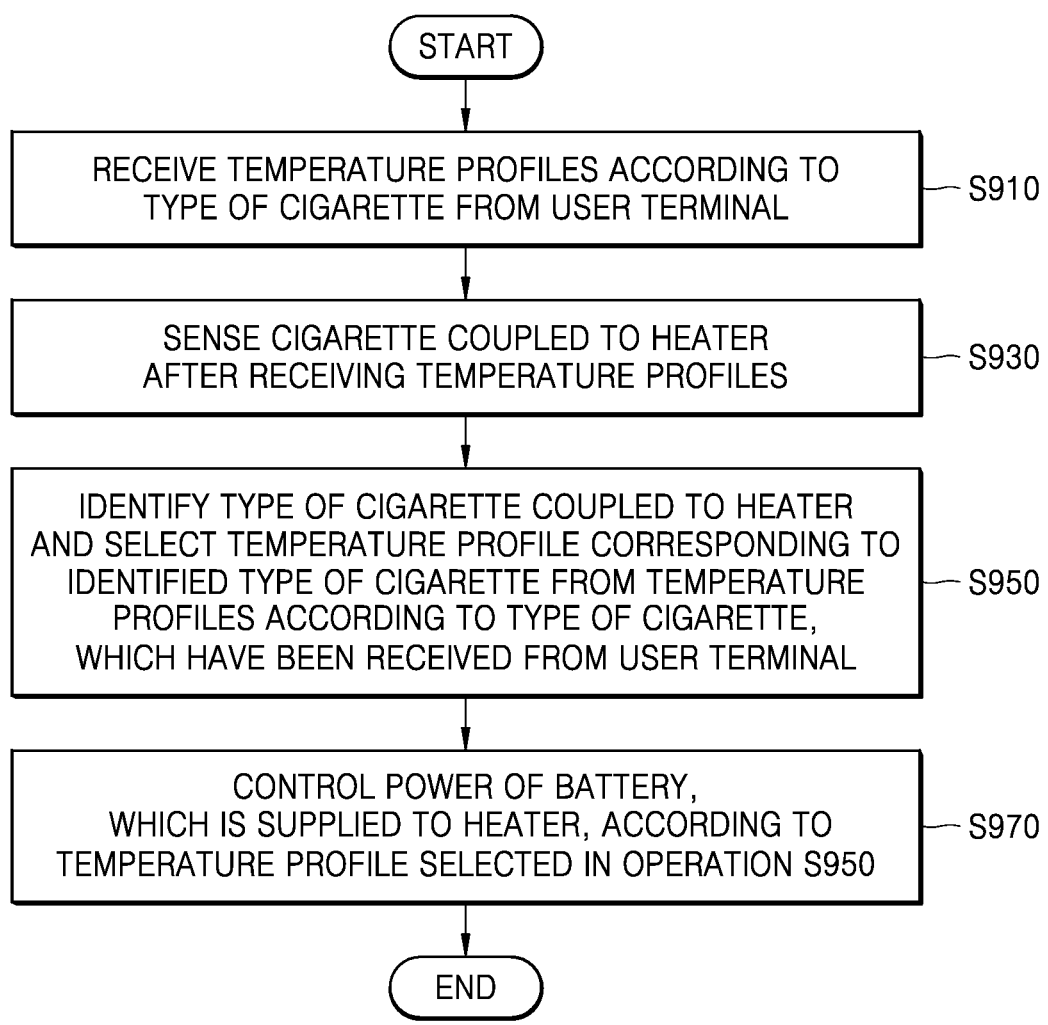
FIG. 9 is a flowchart of an example of a method of controlling the temperature of a heater of an aerosol generation device according to the type of cigarette, according to the present disclosure.

FIG. 9 is a flowchart of an example of a method of controlling the temperature of a heater of an aerosol generation device according to the type of cigarette, according to the present disclosure.

The method of FIG. 9 may be performed by an aerosol generation device including controller 110 of FIG. 7. Therefore, FIG. 7 will be referred to in the description below, and repetitive description in view of the description provided with reference to FIG. 7 will not be omitted.

The profile receiver 111 receives temperature profiles of different types of cigarette from a user terminal in operation S910.

After receiving the temperature profiles, the cigarette sensor 112 senses a cigarette coupled to the heater in operation S930.

The profile selector 113 identifies the type of the cigarette coupled to the heater and selects a temperature profile corresponding to the identified type of the cigarette from the temperature profiles which are received from the user terminal in operation S950.

In operation S970, the power controller 114 controls the power of a battery, which is supplied to the heater, according to the temperature profile selected in operation S950.

According to the method including operations S910 through S970, an aerosol generation device receives and stores temperature profiles of different types of cigarette in advance, and when a cigarette is inserted into the inner space of the aerosol generation device and the aerosol generation device senses that the cigarette is coupled to or contacts a heater, the aerosol generation device controls power supplied to the heater according to a temperature profile corresponding to the cigarette, thereby providing a user with a satisfactory smoking experience.

Figure 10:
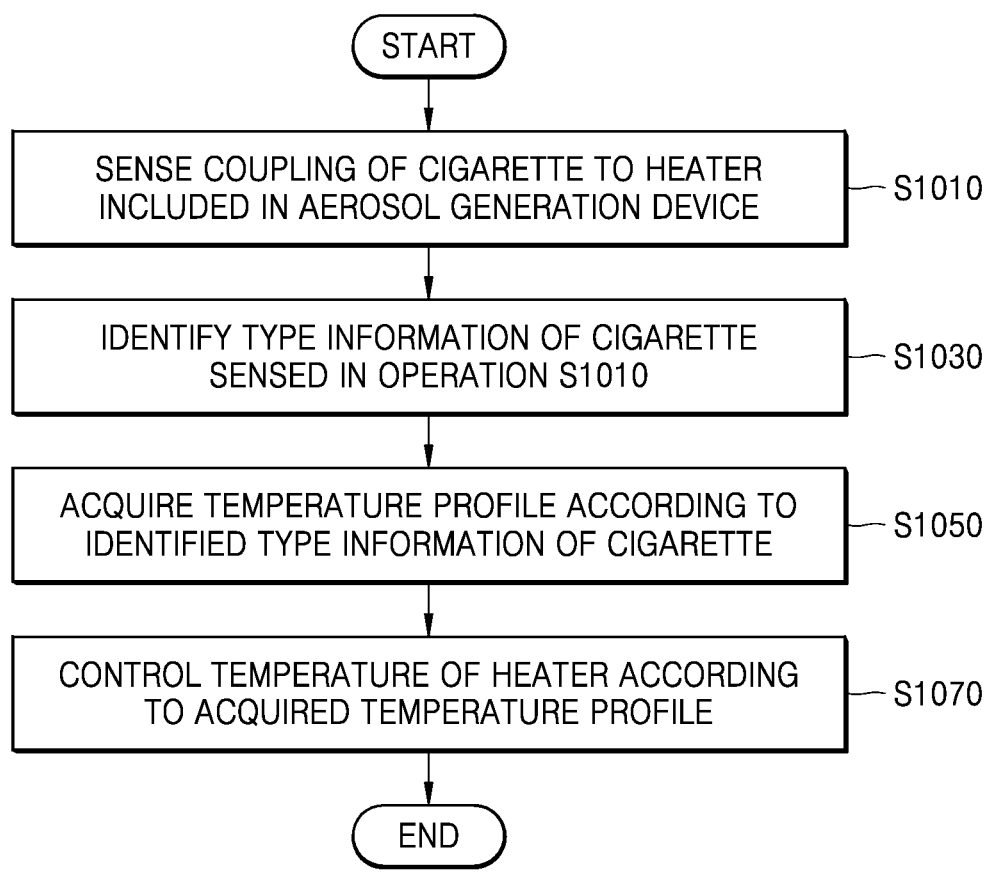
FIG. 10 is a flowchart of another example of a method of controlling the temperature of a heater of an aerosol generation device according to the type of cigarette, according to the present disclosure.

FIG. 10 is a flowchart of another example of a method of controlling the temperature of a heater of an aerosol generation device according to the type of cigarette, according to the present disclosure.

The method of FIG. 10 may be performed by an aerosol generation device including the controller 110 of FIG. 8. Therefore, FIG. 8 will be referred to in the description below, and repetitive description in view of the description provided with reference to FIG. 8 will be omitted.

The cigarette sensor 112 senses coupling of a cigarette to the heater included in the aerosol generation device in operation S1010.

The cigarette identification unit 115 identifies a type of the cigarette sensed in operation S1010 in operation S1030.

In operation S1050, the profile acquisition unit 116 acquires a temperature profile according to the type of the cigarette, which has been identified in operation S1030.

The power controller 114 controls the temperature of the heater according to the acquired temperature profile in operation S1070.

According to the method including operations S1010 through S1070, when a cigarette is inserted into an inner space of an aerosol generation device and the aerosol generation device senses that the cigarette is coupled to or contacts a heater, the aerosol generation device identifies the type of the cigarette, acquires a temperature profile corresponding to the type of the cigarette, and controls power supplied to the heater according to the temperature profile, thereby providing a user with a satisfactory smoking experience. Particularly, in the present exemplary embodiment, the timing for an aerosol generation device to acquire a temperature profile is limited to after a cigarette is inserted into the inner space of the aerosol generation device and coupled to a heater. Accordingly, when the temperature profile in a storage device is updated in real time, a controller of the aerosol generation device may efficiently and functionally control the temperature of the heater based on the newest temperature profile.

FIG. 11 is a flowchart of another example of a method of controlling the temperature of a heater of an aerosol generation device according to the type of cigarette, according to the present disclosure.

In detail, FIG. 11 shows sequential operations of a device, which is physically or logically included in the user terminal 20 in FIG. 1, or an application installed in the user terminal 20. For convenience of description, a subject performing the operations in FIG. 11 is referred to as a smart application.

The smart application receives information about a type of a cigarette coupled to the heater from the aerosol generation device in operation S1110.

The smart application searches a cigarette database for a temperature profile corresponding to the type of the cigarette based on the received information in operation S1130. The cigarette database searched by the smart application in operation S1130 may include a storage device included in the user terminal 20, and the cigarette database 30 which communicates with the user terminal 20 through the communication network 50.

The smart application determines whether the temperature profile corresponding to the type of the cigarette is found in the cigarette database in operation S1150 and transmits the found temperature profile to the aerosol generation device in operation S1170.

An exemplary embodiment of the present disclosure can also be embodied as a computer program executed on a computer using various elements. The computer program may be recorded in a computer readable recording medium. Examples of the computer readable recording medium may include magnetic media such as hard disks, floppy disks, and magnetic tapes; optical media such as CD-ROMs and DVDs; magneto-optical media such as floptical disks; and hardware devices such as read-only memory (ROM), random-access memory (RAM), and flash memory that are specially configured to store and execute program commands.

Meanwhile, the computer program may be specially designed and configured for the present disclosure or may have been known to and usable by those skilled in the field of computer software. Examples of the computer program may include machine codes created by a compiler and high-level language codes that can be executed in a computer using an interpreter.

The particular implementations shown and described herein are illustrative examples of exemplary embodiments and are not intended to otherwise limit the scope of exemplary embodiments in any way. For the sake of brevity, conventional electronics, control systems, software development and other functional aspects of the systems may not be described in detail. Furthermore, the connecting lines or connectors shown in the various figures presented are intended to represent exemplary functional relationships and/or physical or logical couplings between the various elements. It should be noted that many alternative or additional functional relationships, physical connections, or logical connections may be present in a practical device. Moreover, no item of component is essential to the practice of exemplary embodiments unless the element is specifically described as "essential" or "critical."

The use of the terms "a" and "an" and "the" and similar referents in the context of describing exemplary embodiments (especially in the context of the following claims) are to be construed to cover both the singular and the plural. Furthermore, recitation of ranges of values herein is merely intended to serve as a shorthand method of referring individually to each separate value falling within the range, unless otherwise indicated herein, and each separate value is incorporated into the specification as if it were individually recited herein. Also, the steps of all methods described herein can be performed in any suitable order unless otherwise indicated herein or otherwise clearly contradicted by context. Exemplary embodiments are not limited to the described order of the steps. The use of any and all examples, or exemplary language (e.g., "such as") provided herein, is intended merely to better illuminate exemplary embodiments and does not pose a limitation on the scope of exemplary embodiments unless otherwise claimed. It will be apparent to one of ordinary skill in the art that numerous modifications, combinations, and adaptations can be made according to design conditions and factors without departing from the spirit and scope of the attached claims or their equivalents.

It will be understood by one of ordinary skill in the art that various changes in form and details may be made in the exemplary embodiments without departing from the fundamental characteristics thereof. Therefore, the methods described herein should be considered in descriptive sense only and not for purposes of limitation. Therefore, the scope of exemplary embodiments is defined not by the detailed description of exemplary embodiments but by the appended claims, and all differences within the scope will be construed as being included in the present disclosure.

INDUSTRIAL APPLICABILITY

The present disclosure may be used to implement a unit included in a device, such as an electronic cigarette, which generates aerosol inhalable by a user, or implement the device itself.

What is claimed is:

1. A method of controlling a temperature of a heater included in an aerosol generation device, the method comprising:
   receiving temperature profiles of different types of cigarette from a user terminal before a cigarette is coupled to the heater;
   sensing the cigarette coupled to the heater after receiving the temperature profiles, when a distance between the heater and the cigarette becomes less than a predetermined distance that enables the aerosol generation device to detect an identification code on the cigarette;
   identifying a type of the sensed cigarette by detecting the identification code on the cigarette;
   selecting a temperature profile corresponding to the identified type from among the temperature profiles of different types of cigarette that are stored in the aerosol generation device;
   in response to a user input selecting a temperature profile that is different from the selected temperature profile being received, controlling power supplied from a battery to the heater according to the user input; and
   in response to the user input not being received, controlling the power supplied from the battery to the heater to cause the temperature of the heater to match a variable temperature value according to the selected temperature profile.

2. The method of claim 1, wherein the temperature profiles of different types of cigarette are received by the user terminal from a cigarette database for storing the temperature profiles of different types of cigarette.

3. The method of claim 1, wherein the temperature profiles of different types of cigarette received from the user terminal are generated based on information input through an input device of the user terminal.

4. The method of claim 3, wherein the information is input by recognizing one of quick reference (QR) code, bar code, and case code that are attached to a cigarette case.

5. The method of claim 1, wherein the sensing includes sensing the coupling of the cigarette to the heater according to a result of recognizing an optical sticker that is attached to the cigarette.

6. The method of claim 1, wherein the controlling of the power according to the selected temperature profile comprises:
   controlling a pulse width modulator based on the selected temperature profile to supply the power to the heater so that the temperature of the heater varies over time according to the selected temperature profile.

7. A method of controlling a temperature of a heater included in an aerosol generation device, the method comprising:
   sensing coupling of a cigarette to the heater;
   identifying a type of the cigarette;
   in response to sensing the coupling of the cigarette to the heater when a distance between the heater and the cigarette becomes less than a predetermined distance that enables the aerosol generation device to detect an identification code on the cigarette, identifying the type of the cigarette by detecting the identification code on the cigarette, and acquiring temperature profiles of different types of cigarette from a storage device for storing the temperature profiles of different types of cigarette, and identifying a temperature profile corresponding to the type of the cigarette, among the temperature profiles of different types of cigarette;
   in response to a user input selecting a temperature profile that is different from the selected temperature profile being received, controlling the temperature of the heater according to the user input; and
   in response to the user input not being received, controlling the temperature of the heater to vary over time according to the temperature profile corresponding to the type of the cigarette.

8. The method of claim 7, wherein the identifying the type of the cigarette, includes identifying the type of the cigarette using a radio frequency identification (RFID) reader sensing an RFID tag attached to the cigarette.

\* \* \* \* \*